(12) United States Patent
Clausen et al.

(10) Patent No.: US 7,122,317 B2
(45) Date of Patent: Oct. 17, 2006

(54) MULTIPLEX METHOD OF DETECTING SEQUENCE-SPECIFIC DNA BINDING PROTEINS USING DETECTION DUPLEXES COMPRISING UNMODIFIED NUCLEIC ACID SEQUENCES AS CAPTURE TAGS

(75) Inventors: Peter A. Clausen, Ijamsville, MD (US); David P. Carlson, Gaithersburg, MD (US); James G. Lazar, Bethesda, MD (US)

(73) Assignee: Marligen Biosciences, Inc., Ijamsville, MD (US)

( * ) Notice: Subject to any disclaimer, the term of this patent is extended or adjusted under 35 U.S.C. 154(b) by 383 days.

(21) Appl. No.: 10/400,670

(22) Filed: Mar. 28, 2003

(65) Prior Publication Data

US 2003/0215854 A1 Nov. 20, 2003

Related U.S. Application Data

(60) Provisional application No. 60/367,703, filed on Mar. 28, 2002.

(51) Int. Cl.
*C12Q 1/68* (2006.01)
*G01N 33/53* (2006.01)

(52) U.S. Cl. ............................. 435/6; 435/7.1
(58) Field of Classification Search .................... 435/6, 435/7.1
See application file for complete search history.

(56) References Cited

U.S. PATENT DOCUMENTS

| | | | |
|---|---|---|---|
| 5,340,748 A * | 8/1994 | Baugher et al. ............ 436/518 |
| 5,518,885 A | 5/1996 | Raziuddin et al. |
| 5,834,236 A | 11/1998 | Lamb et al. |
| 5,939,261 A | 8/1999 | Loewy et al. |
| 6,265,213 B1 * | 7/2001 | Morgan et al. .......... 435/320.1 |
| 6,284,468 B1 * | 9/2001 | Morgan et al. ................ 435/6 |
| 6,297,013 B1 * | 10/2001 | Morgan et al. ................ 435/6 |
| 6,312,896 B1 | 11/2001 | Heroux et al. |
| 2003/0215854 A1 * | 11/2003 | Clausen et al. ................ 435/6 |

OTHER PUBLICATIONS

Bull et al., Journal of Virology 62(10), 3911-3913 (1988).*
Han et al., J. Biochem. Biophys. Methods 39, 85-92 (1999).*
Ash A. Alizadeh et al., "Distinct types of diffuse large B-cell lymphoma identified by gene expression profiling", Nature, Feb. 3, 2000, pp. 503-511, vol. 3.
Keishiro Aoyagi et al., "Specific Transcription Factors Prognostic for Prostate Cancer Progression", Clinical Cancer Research, Sep. 1998, pp. 2153-2160, vol. 4.
Ana-Maria Bamberger et al., "Expression pattern of the AP-1 family in endometrial cancer: correlations with cell cycle regulators", J. Cancer Res Clin Oncol, 2001, pp. 545-550, vol. 127.
Martin Braddock, "The transcription factor Egr-1: a potential drug in wound healing and tissue repair", The Finnish Medical Society Duodecim, Ann Med, 2001, pp. 313-318, vol. 33.

J-F. M. Brunet et al., "Chemolabeling of Frozen Cerebral Tissue Proteins and Immunopurified Products with Biotin and Digoxigenin: Physicochemical Characteristics of Biotinylated and Digoxigeninated Products", Analytical Biochemistry, 1994, pp. 76-80, vol. 222.
John D. Dignam et al., "Eukaryotic Gene Transcription with Purified Components", Methods in Enzymology, 1983, pp. 582-598, vol. 101.
Alex Elbrecht et al., "Identification by Exonuclease Footprinting of a Distal Promoter-Binding Protein from HeLa Cell Extracts", DNA, 1985, pp. 233-240, vol. 4, No. 3.
E. Ferrannini et al., "Insulin: new roles for an ancient hormone", European Journal of Clinical Investigation, 1999, pp. 842-852, vol. 29.
Jean-Charles Fruchart, PhD., "Peroxisome Proliferator-Activated Receptor-α Activation and High-Density Lipoprotein Metabolism", Am J. Cardiol, Dec. 20, 2001, pp. 24-29, vol. 88, (Suppl.).
R. Jerrold Fulton et al., "Advanced multiplexed analysis with the FlowMetrix™ system", Clinical Chemistry, 1997, pp. 1749-1756, vol. 43, No. 9.
Shin-Ichi Fujimaki et al., "Decreased expression of transcription factor GATA-2 in haematopoietic stem cells in patients with aplastic anaemia", British Journal of Haematology, 2001, pp. 52-57, vol. 113.
Todd S.-C. Juan et al., "Participation of the transcription factor C/EBPδ in the acute-phase regulation of the human gene for complement component C3", Proc. Natl. Acad. Sci. USA, Apr. 1993, pp. 2584-2588, vol. 90.
Sander Kersten, "Mechanisms of nutritional and hormonal regulation of lipogenesis", EMBO Reports, 2001, pp. 282-286, vol. 2, No. 4.
Yoshiaki Kido et al., "The Insulin Receptor and Its Cellular Targets", The Journal of Clinical Endocrinology & Metabolism, 2001, pp. 972-979, vol. 86, No. 3.
Che-Fu Kuo et al., "Structure and Function of the DNA Repair Enzyme Exonuclease III from *E. coli*", Annals New York Academy of Sciences, 1994, pp. 223-234, vol. 726.
Robert Lam et al., "An array-based method for specifically profiling multiple transcription factor activity", American Biotechnology Laboratory, Jul. 2002, pp. 22 and 26.

(Continued)

*Primary Examiner*—Kenneth R. Horlick
(74) *Attorney, Agent, or Firm*—Proskauer Rose LLP

(57) ABSTRACT

Compositions and methods are provided for detecting and measuring DNA-binding proteins. The compositions and methods permit the simultaneous or near-simultaneous detection of multiple DNA-binding proteins in a multiplex or array format, and can be used to generate profiles of DNA binding activity by proteins, specifically, transcription factors. Multiple protein-DNA binding events in a single sample may be detected and quantitated in a high-throughput format.

9 Claims, 14 Drawing Sheets

OTHER PUBLICATIONS

Ryuichi Morishita et al., "Gene therapy in vascular medicine: recent advances and future perspectives", Pharmacology & Therapeutics, 2001, pp. 105-114, vol. 91.

Lawrence J. Peck et al., "Bead-shift isolation of protein-DNA complexes on a 5S RNA gene", Nucleic Acids Research, 1994, pp. 443-449, vol. 22, No. 3.

George I. Salti et al., "Micropthalmia Transcription Factor: A New Prognostic Marker in Intermediate-thickness Cutaneous Malignant Melanoma", Cancer Research, Sep. 15, 2000, pp. 5012-5016, vol. 60.

Dari Shalon et al., "A DNA Microarray System for Analyzing Complex DNA Samples Using Two-color Fluorescent Probe Hbridization", Genome Research, 1996, pp. 639-645.

Z. Shen et al., "Multiple Transcription Factor Profiling by Enzyme-Linked Immunoassay", Biotechnologies, 2002, pp. 1168-1177, vol. 32, No. 5.

S. Skulstad et al., "Labeling of surface proteins of herpes simplex virus type 1 using a modified biotin-streptavidin system", Virus Research, 1995, pp. 253-270, vol. 37.

Michael B. Sporn et al., "Prospects for prevention and treatment of cancer with selective PPARymodulators (SPARMSs)", Trends in Molecular Medicine, Sep. 2001, pp. 395-400, vol. 7, No. 9.

Szybalski et al., "Class-IIS restriction enzymes—a review", Gene, 1991, pp. 13-26, vol. 100.

Iwao Takanami et al., "Expression of Ets-1 Is Correlated with Urokinase- Type Plasminogen Activator and Poor Prognosis in Pulmonary Adenocarcinoma", Tumor Biol., 2001, pp. 205-210, vol. 22.

Wei-Qin Zhao et al., "Role of insulin and insulin receptor in learning and memory", Molecular and Cellular Endocrinology, 2001, pp. 125-134, vol. 177.

* cited by examiner

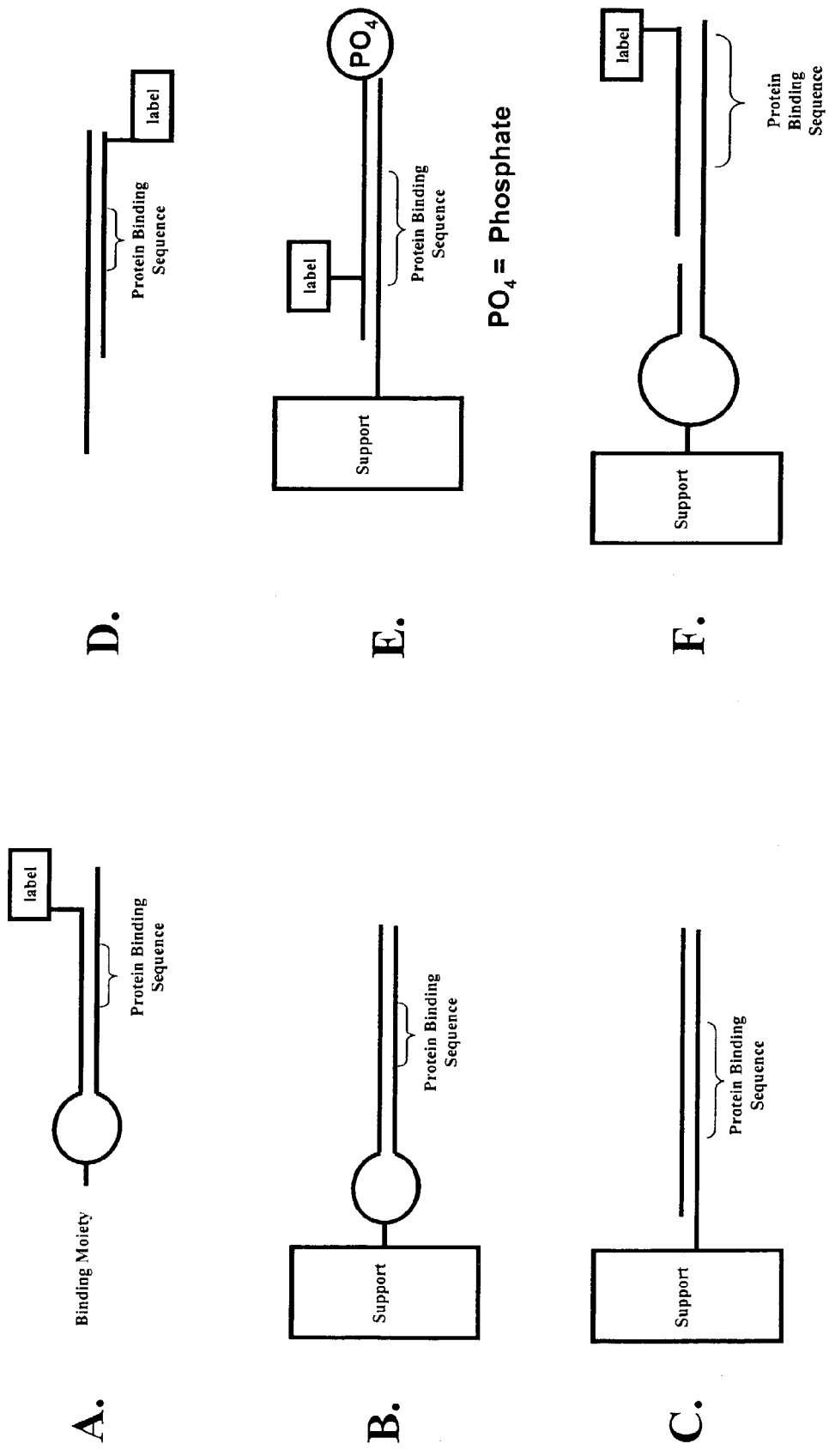
Figure 1. Examples of Detection Duplexes

Figure 2. Properties of External Cleavage Reagents

| Enzyme | Polarity | DNA substrate | | Structure | | | | | Products Produced |
|---|---|---|---|---|---|---|---|---|---|
| | | ss | ds | 5' PO₄ | 5'ext | 3'ext | blunt | nick | |
| Lambda Exonuclease | 5'→3' | +/- | + | Yes | +/- | + | + | - | ss DNA, dNMP |
| T7 Exonuclease | 5'→3' | - | + | No | +/- | + | + | + | ss DNA, dNMP, dinuc |
| Exonuclease III | 3'→5' | - | + | No | + | +/- | + | + | ss DNA, dNMP |
| Exonuclease I | 3'→5' | + | - | No | - | +/- | +/- | NR | dNMP, dinucleotide |
| Exonuclease T | 3'→5' | + | - | No | - | + | +/- | NR | dNMP |
| BAL-31 Nuclease | 3'→5' | + | + | No | + | + | + | + | ss DNA, dNMP |

MULTIPLEX METHOD OF DETECTING SEQUENCE-SPECIFIC DNA BINDING PROTEINS USING DETECTION DUPLEXES COMPRISING UNMODIFIED NUCLEIC ACID SEQUENCES AS CAPTURE TAGS

This application claims priority to U.S. Ser. No. 60/367,703, filed Mar. 28, 2002. The entirety of this application is hereby incorporated by reference.

BACKGROUND OF THE INVENTION

1. Field of the Invention

This invention provides compositions and methods for profiling transcription factor activity. In particular, the invention provides nucleic acid constructs containing protein binding sites and methods for detecting and measuring the binding of proteins and particularly transcription factors to the binding sites in these constructs.

2. Background and Related Art

Eukaryotes are composed of specialized cell types that are organized into tissues and organs. Regardless of cell type and function, all cells within an individual eukaryotic organism contain the same set of genes referred to as the genome. Differences between cells arise through the differential expression of genes. Expression of individual genes is controlled through the binding of proteins to regulatory sequences of DNA in the genome such as promoters and repressors. Protein binding to such control sequences can cause an increase or decrease in the rate of transcription of a gene. These DNA-binding proteins, called transcription factors, regulate gene transcription and thereby control all of the essential characteristics of a cell including cellular reproduction, development and differentiation, response to environmental stimuli, and tissue homeostasis in normal and disease states. Transcription factors comprise hundreds of specialized proteins that regulate gene expression by either facilitating or inhibiting the enzyme RNA polymerase in the initiation and maintenance of transcription.

The activation or inhibition of regulatory transcription factors occurs as a downstream event in signal transduction cascades that are initiated by perturbations such as a change in the oxidation state of a cell, or the binding of a ligand to its cell surface receptor. In the case of cell surface receptors, a ligand-binding event may trigger signaling cascades that fan out to regulate multiple genes that contribute to biological responses. Cross talk between signal transduction systems also is common, with disparate stimuli utilizing many of the same protein kinases, phosphatases and second messenger systems. Highly refined regulation of biological responses, therefore, occurs as webs of interacting signaling systems involving kinases, phosphatases and second messengers triggered by each stimulus that culminate in qualitatively and/or quantitatively different sets of transcription factor activation. It has been estimated that there are approximately 1000 transcription factors in the human genome that contribute the specificity to regulate the independent expression of approximately 40,000 genes. Consequently, biological responses that are characterized by changes in gene expression may be defined by distinct signatures of transcription factor activation. Transcription factors, therefore, are of significant interest as targets to affect specific individual or global changes in gene expression.

Cell surface receptors have been a primary focus of pharmaceutical research and comprise the majority of therapeutic targets. These receptor-targeted strategies have been successful in treating disease and prolonging life, but most of these therapies suffer from a lack of specificity. In the majority of cases, cell surface receptors are multifunctional. For instance, a given receptor may reside on different cell types, and activate intricate webs of signaling cascades to regulate multiple biological responses. A well-characterized example of the multi-functional nature of receptors is the insulin receptor. Insulin receptors are broadly distributed in diverse tissues and activate multiple second messenger systems to directly affect metabolic responses ranging from glucose homeostasis to lipolysis, platelet aggregation, and more recently, the formation of memory (1–3).

The consequence of a multifunctional role for individual receptors is that many drugs on the market today have detrimental side effects that exact an enormous cost on society and the pharmaceutical industry. The need to better define biological responses to potential therapeutic agents and to more fully understand the nature of potential therapeutic targets has spurred great interest in the development and application of DNA microarrays for comparative gene analysis.

The result of this interest has been many advancements and successes using gene chip technology. By screening tens of thousands of genes on DNA microarrays, patterns or profiles of gene expression comprising up to several hundred genes have been used to diagnose and classify specific diseases (5). Nonetheless, obtaining profiles of gene expression that increase understanding of disease processes has proven difficult in many cases due to the complexity of the diseases.

In these circumstances, profiling transcription factor activity may provide an alternative means to diagnose and classify disease. In contrast to results obtained from gene expression profiling of mRNA, reports have demonstrated that significant qualitative and quantitative differences in transcription factor activation are associated with and may control the expression of disease-associated genes responsible for the onset and progression of infectious diseases, autoimmune, inflammatory, neurological, circulatory (14) and cardiovascular diseases (15,17), obesity (18) and cancer (15,16,19). Transcription factors have been demonstrated to have diagnostic (5) and prognostic (6) applications and have been identified as targets for therapeutic intervention into cancer and inflammatory diseases (4). Unfortunately, progress in transcription factor targeted therapy and transcription-factor based diagnostic and prognostic application has been slow due to the bottleneck that exists for screening large numbers of samples for multiple transcription factors. Currently, no technology is available for the rapid comprehensive profiling of the activity of multiple transcription factors.

Conventional methods of detecting and measuring DNA-binding proteins such as transcription factors include the electrophoretic mobility shift assay (EMSA) (24), supershift EMSA (25), and ELISA-based techniques. The EMSA or gel-shift assay provides a simple and rapid method for detecting DNA-binding proteins such as transcription factors, and has been widely used. The assay is based on the observation that complexes of protein and DNA migrate through a non-denaturing polyacrylamide gel more slowly than free DNA fragments or double-stranded oligonucleotides. The EMSA is performed by incubating a purified protein, or a complex mixture of proteins (such as nuclear or whole cell extract preparations), with a labeled DNA fragment containing the putative protein binding site. The reaction products are then analyzed by electrophoresis on a nondenaturing polyacrylamide gel. The specificity of the DNA-binding protein for the putative binding site is established by performing competition experiments using DNA fragments or oligonucleotides containing a binding site for the protein of interest or other unrelated DNA sequences. Gel-shift assays typically use radioactively-labeled DNA probes, but non-radioactive labels such as biotin or fluorescent dyes can also be used. This method is not suited, however, for rapid screening of large numbers of samples or multiple transcription factors simultaneously.

The supershift-EMSA is a complement to the gel shift assay that allows specific identification of the DNA-bound protein using specific antibodies. The supershift-EMSA is performed by incubating a purified protein, or a complex mixture of proteins (such as nuclear or whole cell extract preparations), with a labeled or unlabeled DNA fragment containing the putative protein binding site and an antibody to the putative protein. The reaction products are then analyzed by electrophoresis on a non-denaturing polyacrylamide gel and the DNA-protein-antibody complex can be detected by detecting the label on the DNA or by using an antibody to detect the antibody in the DNA-protein-antibody complex. Again, the specificity of the DNA-binding protein for the putative binding site is established by competition experiments using DNA fragments or oligonucleotides containing a binding site for the protein of interest or other unrelated DNA sequences. The "super-complex" of DNA-protein-antibody has significantly reduced mobility than the DNA-protein complex when subjected to electrophoresis in non-denaturing gels. Although useful for basic research, gel-shift and supershift assays have low sensitivity and very low throughput due to the large amount of handling that must be performed. Furthermore, the gel-shift and supershift assays are not quantitative and can only detect the presence or absence of a particular DNA-binding protein.

Recently, ELISA techniques have become available for detection of known DNA-binding proteins (22). In these ELISA assays, DNA fragments containing a putative protein binding site are bound to a solid phase such as the bottoms of the wells of a 96-well polystyrene plate. The sample containing a purified protein, or a complex mixture of proteins (such as nuclear or whole cell extract preparations) is incubated in the well containing the immobilized DNA fragment containing the putative protein binding site. The well is then washed to remove all non-bound components of the sample, and an antibody specific for the putative bound protein is added. Binding of the antibody is accomplished using standard ELISA techniques with colorimetric, fluorescent, or chemiluminescent detection.

ELISA assays are roughly 10-fold more sensitive than gel-shift assays and can be adapted to high-throughput analysis. However, they suffer a major disadvantage in that the target protein binding sequences must be known, and antibodies must be available to detect the bound protein. Thus, they are limited to studying systems that have already been well-characterized. Furthermore, these assays cannot be multiplexed and, accordingly, the sample volume required to obtain a panel of DNA-binding markers precludes the broad use of this technique for generating DNA-protein binding profiles.

A multiplex transcription factor assay based on a combination of gel shift and DNA chip technology has also been recently described (23). In this assay a nuclear extract is incubated with a pool of biotin-labeled double-stranded oligonucleotides. The protein-bound oligonucleotides are electrophoresed, and the portion that have gel-shifted are excised from the gel and eluted. The sequences of the oligonucleotides are then determined by hybridization to a membrane array. Although this technique is multiplexed and can provide a transcription factor profile, it involves multiple steps and requires many manipulations that must be performed by hand it and therefore is unsuitable for moderate or high-throughput analysis.

It is apparent, therefore, that compositions and methods that permit simultaneous detection of multiple DNA-binding proteins in a multiplex or array format, and that provide profiles of DNA binding activity by proteins, specifically, transcription factors, are greatly to be desired. In particular, it is highly desirable to develop assays that allow detection and measurement of multiple protein-DNA binding events in a single sample.

The present invention therefore provides novel compositions and assay methods that permit specific detection of DNA-binding proteins. In particular, the present invention represents a substantial improvement over the prior art in that it provides a quantitative output without the need for specific antibodies or protein binding reagents. Furthermore, the present invention does not result in the release of a soluble signaling molecule so that detection of DNA-binding proteins can be performed in a solid- or liquid-array format, thereby facilitating the use of signal amplification techniques that cannot be used when a soluble signal is generated.

SUMMARY OF THE INVENTION

Accordingly, it is an object of the present invention to provide methods and compositions for detecting sequence specific DNA binding proteins.

It is a further object of the invention to provide methods for the simultaneous detection of a plurality of sequence specific DNA binding proteins, such as transcription factors.

In accordance with this object of the present invention, there is provided a method for detecting sequence specific DNA binding proteins, comprising (a) contacting a detection duplex with a sample suspected of containing at least one sequence specific DNA binding protein for a time sufficient to permit sequence-specific binding between said duplex and said binding protein; (b) contacting the mixture from step (a) with a cleavage reagent that is capable of cleaving the detection duplex, where cleavage of the detection duplex is inhibited by binding of said DNA binding protein to the duplex; and (c) detecting the inhibition of cleavage by the DNA binding protein. The cleavage reagent may be a sequence specific cleavage reagent, such as a restriction endonuclease, and the detection duplex may comprise a restriction endonuclease recognition site. The restriction endonuclease may be a Type II or Type IIs restriction endonuclease and the restriction endonuclease recognition site may be is a Type II or Type IIs restriction endonuclease recognition site respectively. The cleavage reagent also may be an exonuclease that lacks significant endonuclease activity.

In these methods, the detection duplex may comprise (i) a first oligonucleotide comprising a tag sequence and (ii) a second oligonucleotide that is complementary to the first oligonucleotide, where the second oligonucleotide comprises a detectable label. The detection duplex may further comprise a capture tag. The detection duplex may be immobilized on a solid support via the capture tag prior to contacting with the sample. A plurality of detection duplexes may be used, where each detection duplex carries a capture tag that permits capture of the duplex at a predetermined position on a solid surface.

In accordance with another object of the present invention, there is provided a method a method for detecting sequence specific DNA binding proteins, comprising (a) contacting a sample suspected of containing at least one sequence specific DNA binding protein with a detection duplex for a time sufficient to permit sequence-specific binding between said duplex and the binding protein; and (b) detecting binding between the duplex and the binding protein. The duplex may be immobilized on a solid support before or after step (a) or (b). Immobilization may occur via a capture tag on the duplex. Detection may be achieved by labeling the protein sample with a detectable label prior to contacting with the detection duplex. Detection may be achieved via a detection reagent that specifically binds said binding protein, such as an antibody. In this method, the detection duplex may be labeled, and the immobilizing step can be achieved via capture of the binding protein onto a surface.

In accordance with another aspect of the invention there is provided a method for detecting sequence specific DNA binding proteins, comprising: (a) contacting a capture surface with a sample suspected of containing at least one sequence specific DNA binding protein, for a time sufficient to permit capture of said sequence-specific binding protein on the capture surface; (b) contacting the capture surface with a detection duplex, and (c) detecting binding between the duplex and the binding protein.

The invention described herein addresses the unmet need for a high-through-put multiplex assay for profiling transcription factor activity. The invention provides advantages over currently available technologies for profiling the activity of transcription factors.

Further objects, features, aspects, uses and advantages of the present invention will become apparent from the detailed description of preferred embodiments that follows.

BRIEF DESCRIPTION OF THE DRAWINGS

FIG. 1 shows examples of Detection Duplexes. All detection duplexes contain a protein-binding sequence. The detection duplex may be completely double-stranded or may be partially single-stranded and partially double-stranded and may contain gaps and nicks. The detection duplex may be constructed of one or more oligonucleotides and may comprise one or more self-hybridized regions that form hairpin loops. The detection duplex may contain any combination of natural and non-natural nucleotides and may contain non-natural linkages between nucleotides. The detection duplex may comprise one or more detectable labels and one or more binding moieties. The detection duplex may be immobilized on a support or may be capable of being immobilized on a support through a binding moiety or through hybridization of a single-stranded portion of the detection duplex to a complementary sequence on the support. The detection duplex may also contain intentional or unintentional mismatches. The detection duplex may comprise other entities such as peptides, carbohydrates and the like.

FIG. 2. Properties of External Cleavage Reagents. This figure summarizes the properties of some of the external cleavage reagents of the present invention. Polarity describes the direction of digestion. Substrate describes the enzymes preference for single-stranded (SS) or double-stranded (DS) DNA. Structure denotes the particular nucleic acid structures that are compatible with each enzyme: "5' PO4" denotes whether or not a 5' phosphate is required for enzyme activity, "5' ext" denotes whether or not the enzyme will digest a DNA with a 5' extension, "3' ext" denotes whether or not the enzyme will digest DNA with a 3' extension, "blunt" denotes whether or not the enzyme has activity on blunt-ended DNA fragments and "nick" denotes whether the enzyme will digest beginning at a nick in double-stranded DNA.

If no protein has bound to the protein binding sequence (FIG. 7), then lambda exonuclease will digest the first DNA strand down to the support and the second DNA strand that was hybridized to the first strand will be released since there no longer is a complementary strand for it to hybridize with. When the mixture is heat denatured and washed, the second DNA strand and the digested first strand are both washed away leaving nothing remaining for the labeled oligonucleotide or nucleic acid to bind to. Accordingly, no label will be detected.

Figure 8:
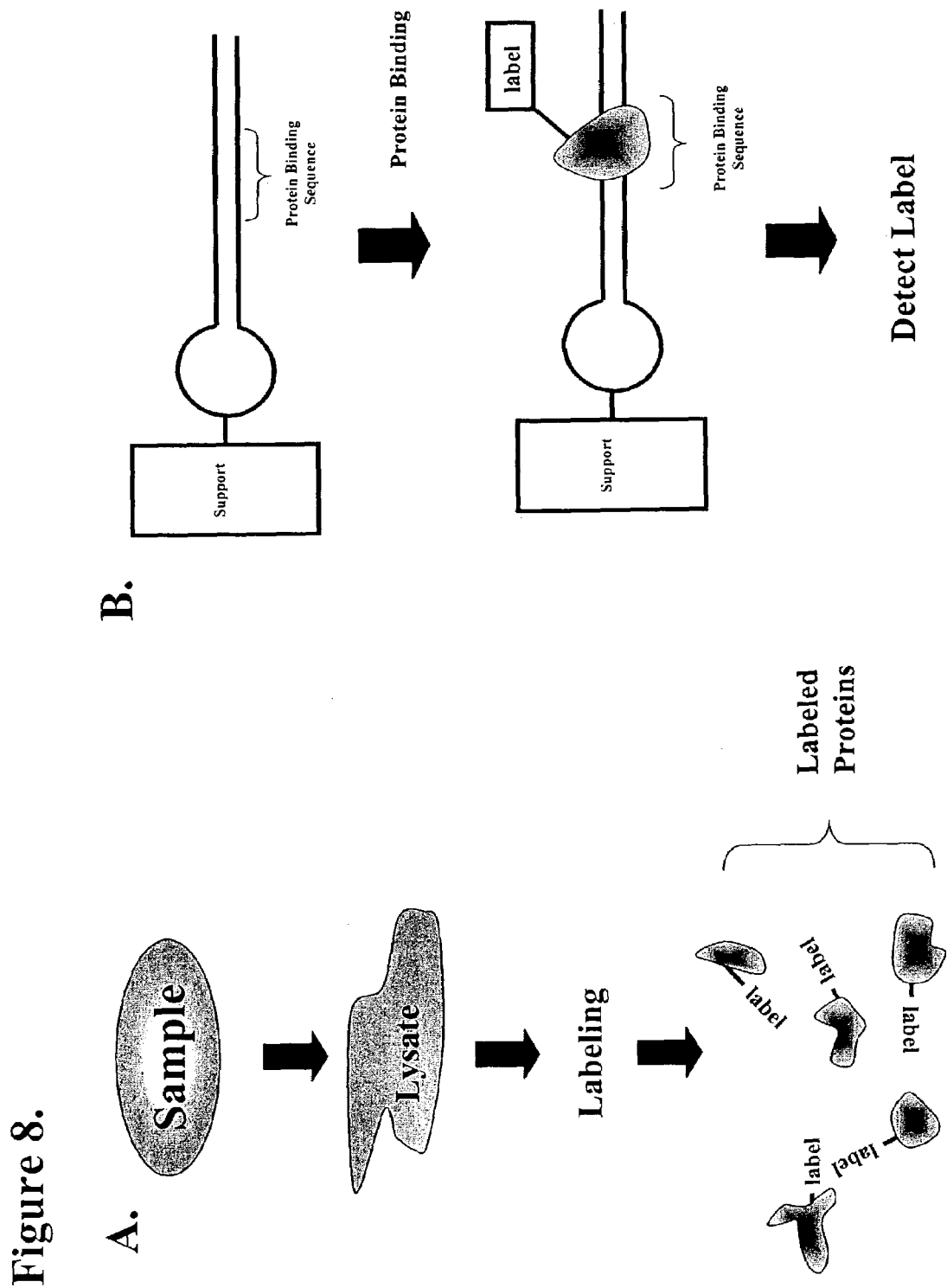

FIG. 8. This figure illustrates the detection of protein binding to DNA through the binding of labeled proteins to a detection duplex. In this example, the components of the sample are labeled with a reactive label moiety such as N-hydroxysuccinimide derivatives of biotin or fluorescent dyes such as Cy3 or Cy5 (Amersham Biosciences). After labeling, the labeled proteins are brought into contact with the detection duplex on a support. After washing away unbound material, proteins that bind to the protein binding sequence on the detection duplex are detected via the label that is now bound to the support. Alternatively, the labeled proteins can be contacted with the detection duplex in solution, and the detection duplex can be subsequently captured onto a support.

Figure 9:
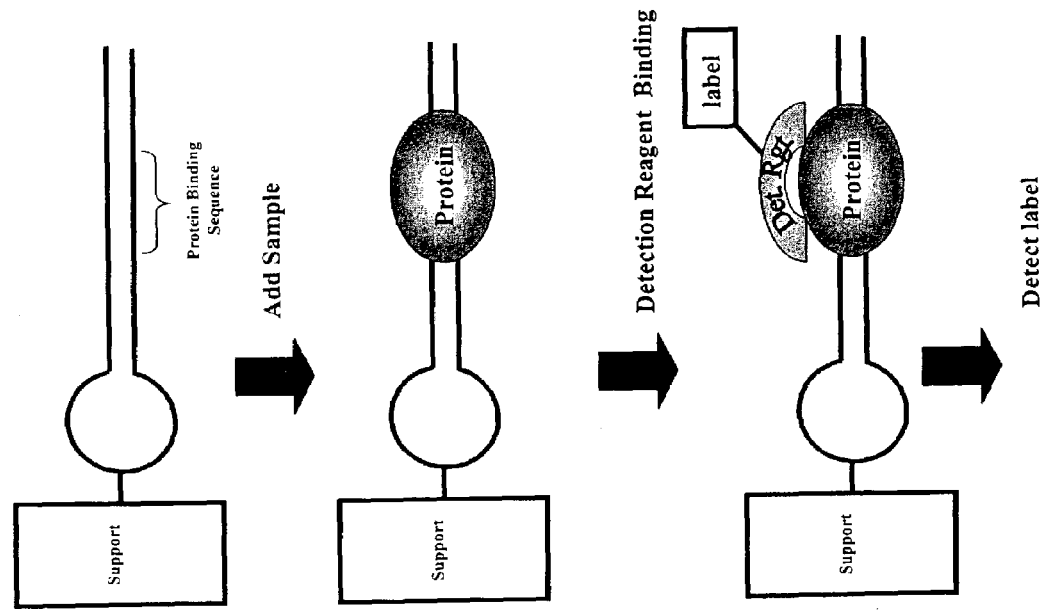

FIG. 9. This figure illustrates the detection of protein binding to detection duplexes through the use of detection reagents to detect the proteins bound to the detection duplex. In this example, the sample is reacted directly with an immobilized detection duplex and proteins are allowed to bind to the protein-binding sequence. The bound proteins are subsequently detected with a detection reagent that may consist of, for example, antibodies directed against specific proteins, antibodies directed against general classes of proteins, antibodies directed against specific biochemical motifs such as phosphotyrosine, or a mixture of antibodies to many proteins, classes or motifs. Alternatively, the bound proteins may be detected with other biochemicals such as proteins known as SH2 domains or other recombinant or synthetic protein amino acid that bind to the proteins bound to the DNA. Alternatively, chemical stains may be used to detect the proteins bound to the DNA. Such stains may change color when bound to certain types of proteins or binding of the stain to certain types of proteins may induce a change from a non-fluorescent state to a fluorescent state (for example, the PhosPhoQ protein stain from Pierce stains only phosphorylated proteins).

Figure 10:
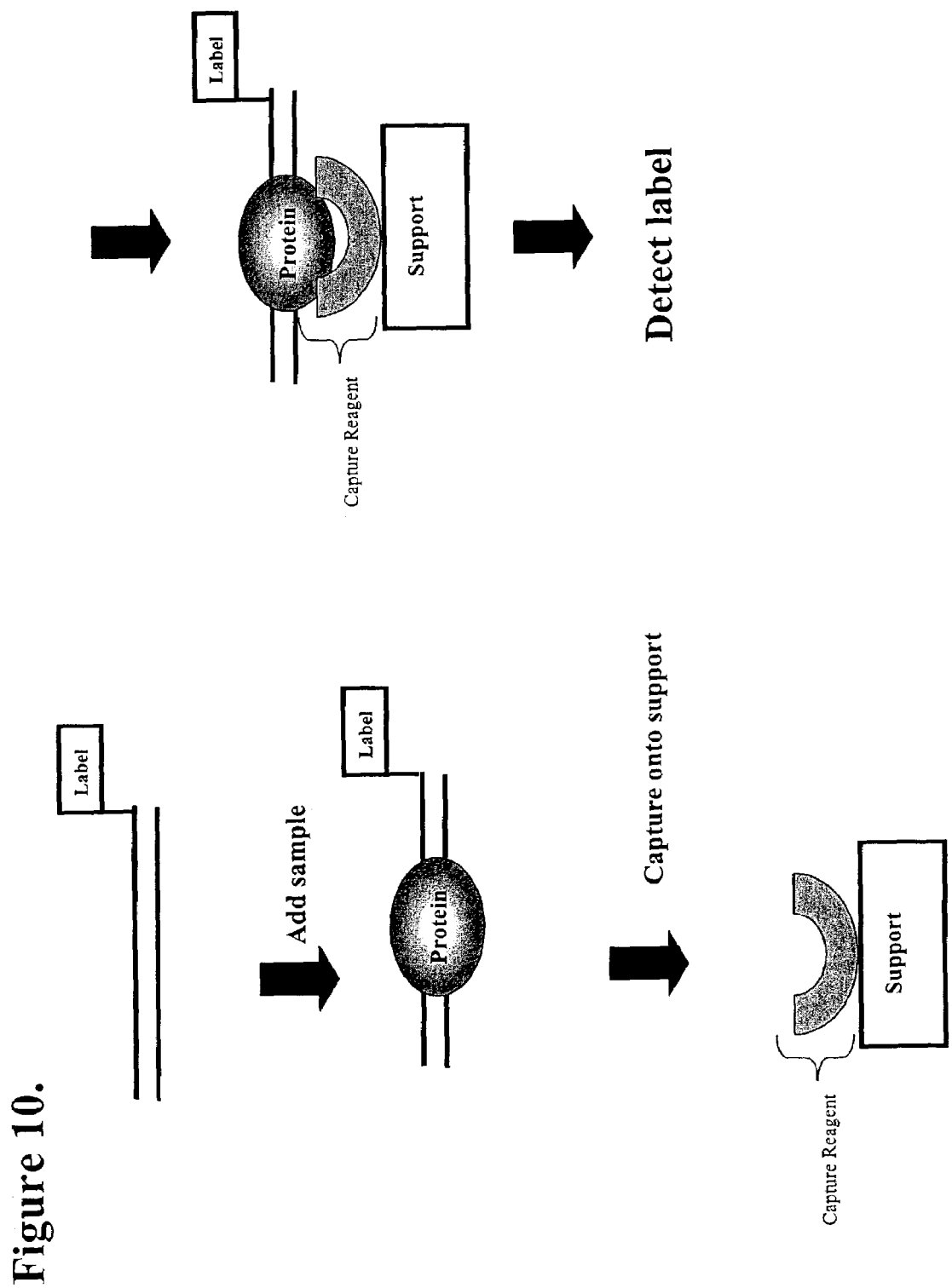

FIG. 10 illustrates the detection of protein binding to detection duplexes through a capture reagent. In this example, a labeled detection duplex is added to the sample and proteins are allowed to bind to the detection duplex. Protein-duplex complexes are then captured onto a support that has been modified to comprise a capture reagent on its surface. After the complexes have been capture, the label on the detection duplex is detected. In this format, for example, the capture reagent could be an antibody specific for the protein.

Figure 11:
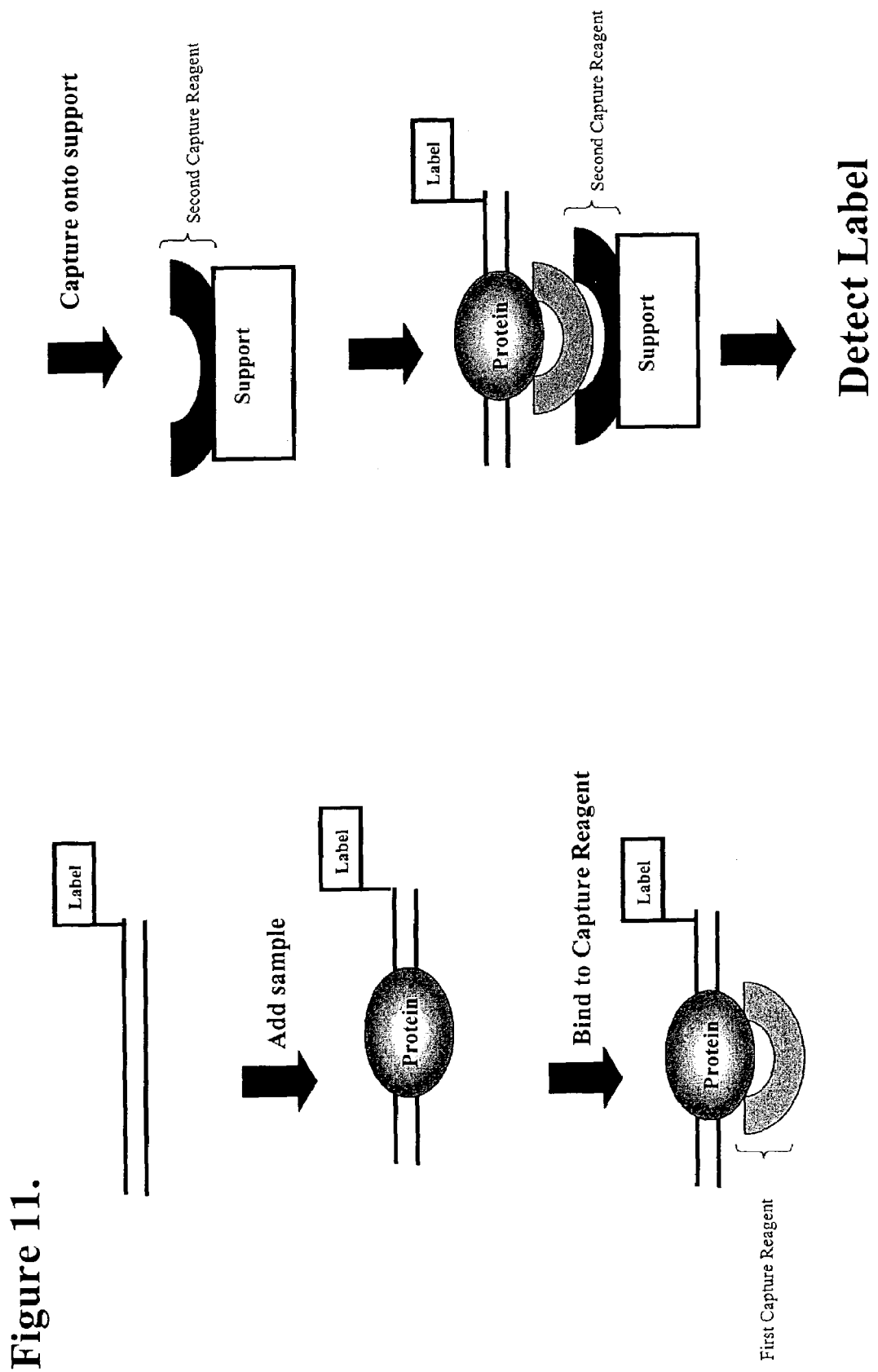

FIG. 11 figure illustrates the detection of protein binding to detection duplexes through a capture reagent. In this example, a labeled detection duplex is added to the sample and proteins are allowed to bind to the detection duplex. A first capture reagent is then added that binds to the protein component of the protein-duplex complexes. These first capture reagent-protein-duplex complexes are then captured onto a support that has been modified to comprise a second capture reagent on the surface. After the complexes have been captured, the label on the detection duplex is detected. In this format, for example, the first capture reagent could be a goat polyclonal antibody specific for the protein and the second capture reagent could be an antibody specific reagent such as Protein G.

Figure 12:
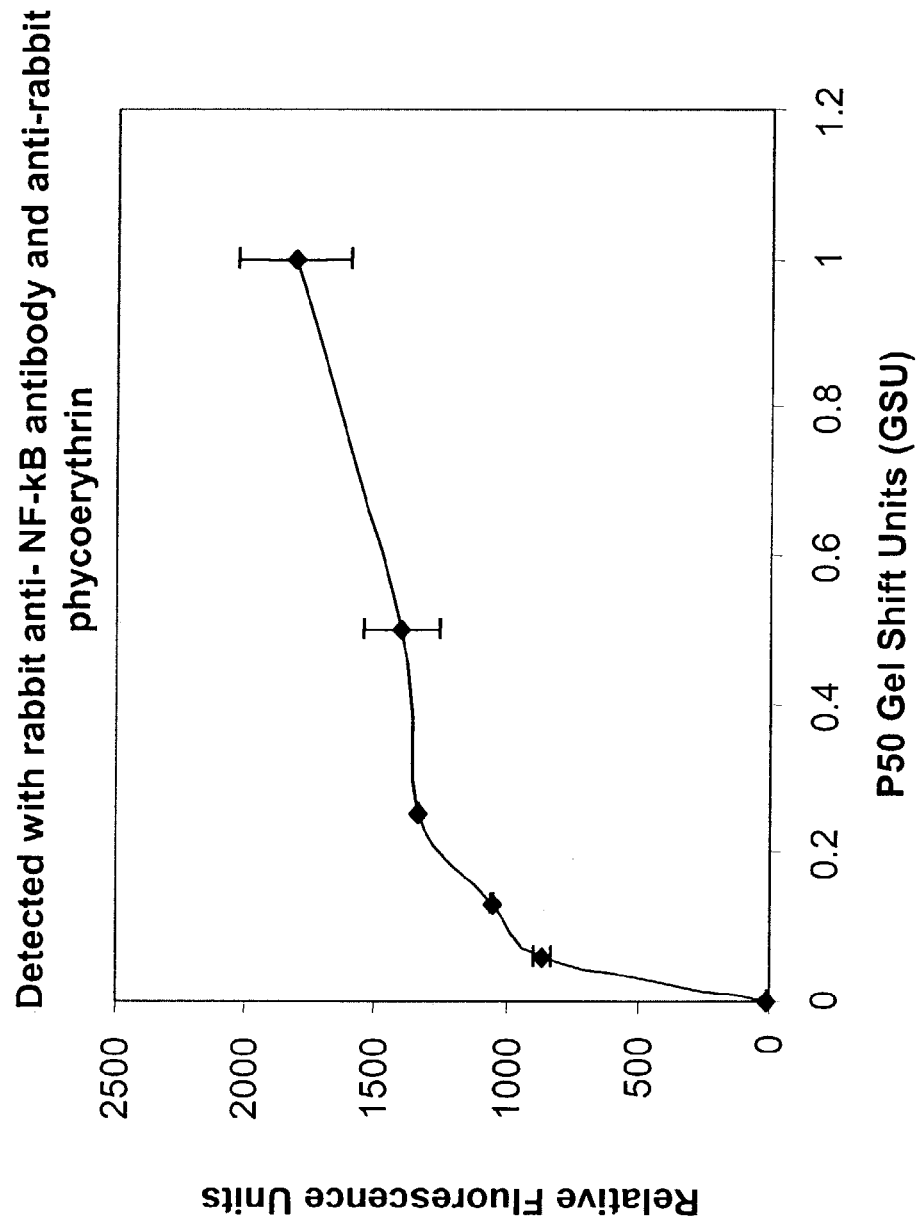

FIG. 12 shows results of an experiment demonstrating the detection of protein binding to detection duplexes with Detection Reagents. A detection duplex containing a capture tag was created by annealing 2 oligonucleotides. The detection duplex thus formed contained an NF-kb p50 binding site and a capture tag sequence. The detection duplex was incubated with a range of concentrations of the NF-kB p50 protein and was then captured onto beads by hybridization of the capture tag to a complementary oligonucleotide bound to the bead. Bound protein was detected using a rabbit antibody to the NF-kB p50 protein followed by a phycorerythrin-labeled anti-rabbit antibody. Fluorescent signal on the beads was measured in a Luminex 100 flow cytometer.

Figure 13:
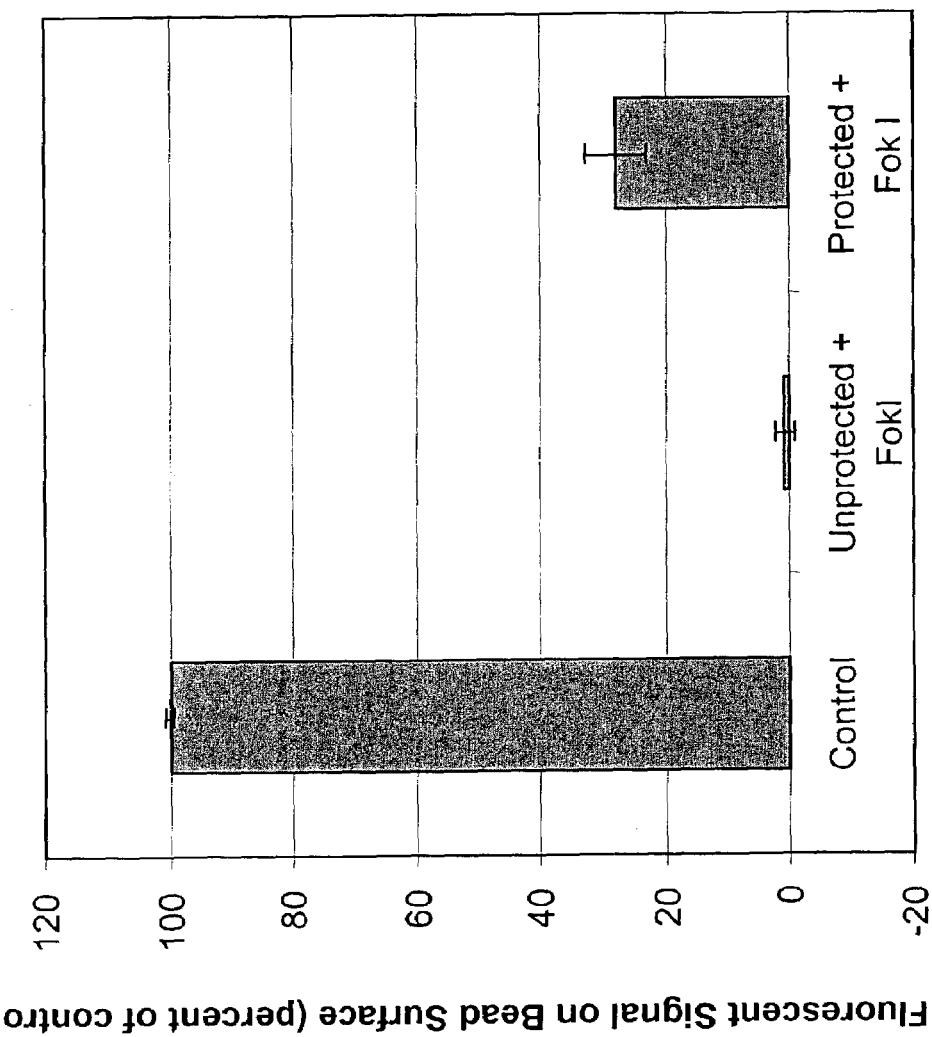

FIG. 13 shows detection of NF-kB p50 DNA binding protein by protection of the detection duplex from digestion by the class IIs restriction enzyme Fok I. In this example a detection duplex was used that comprised a capture tag, a label, a protein binding site and a Fok I binding site. The detection duplex comprised a Fok I binding site and an NF-KB p50 binding site such that the Fok I would cleave the DNA within the p50 binding site. A biotin label was synthesized into the detection duplex such that the biotin label would be released if the duplex was cleaved by the Fok I. The detection duplex was incubated with and without NF-KB protein. Fok I enzyme was added and allowed to incubate. The detection duplexes were then captured onto beads by hybridization of the capture tag to complementary oligonucleotides bound to the beads. The biotin label was detected with a streptavidin-phycoerythrin conjugate. The sample that was incubated with p50 protein gave substantial signal while the sample with no p50 protein gave almost no signal, indicating that the binding of the p50 protein protected the duplex from digestion by the Fok I enzyme.

Figure 14:
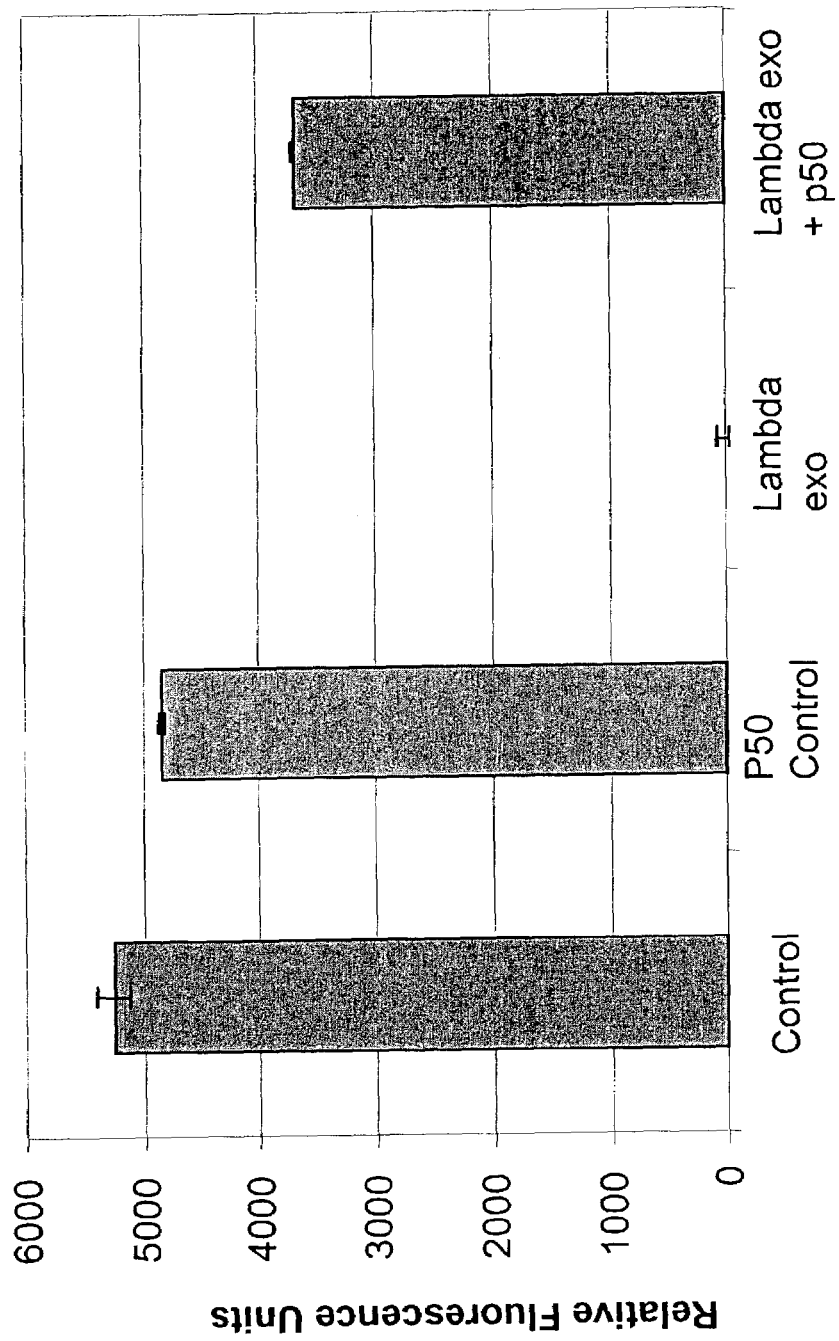

FIG. 14. Detection of NK-kB p50 protein by protection of the detection duplex from digestion by lambda exonuclease. In this example, the detection duplex comprised a protein binding sequence, a biotin label, and a 5' phosphate moiety on the 5' end of one of the DNA strands coupled to polystyrene beads. After coupling, detection duplexes coupled to beads were incubated with and without NF-kB p50 protein. Subsequently, lambda exonuclease was added and incubated to allow the enzyme time to digest the DNA strand labeled with the 5' phosphate group. Following digestion, streptavidin-phycoerythrin conjugate was added to detect the biotin label remaining on the detection duplex coupled to the beads. In the absence of p50 protein, the detection was completely digested away while in the presence of p50 protein, a signal of approximately 3600 fluorescent units was measured demonstrating that p50 could be detected by its ability to inhibit the activity of lambda exonuclease on a detection duplex.

DETAILED DESCRIPTION OF THE INVENTION

The invention provides methods and compositions for detecting and identifying sequence-specific nucleic acid binding proteins in a sample. The sample may be any sample, such as a cellular or tissue extract, that is suspected of containing such binding proteins. The methods and compositions may be used for detecting any protein that binds to nucleic acids in a sequence-specific manner. Examples of such proteins include, but are not limited to, eukaryotic transcription factors. The methods are suitable for the rapid and sensitive multiplex detection of nucleic acid binding proteins.

The methods involve either a cleavage-based mechanism or a protein recognition element-based mechanism. In the cleavage-based mechanism, a labeled detection duplex is contacted with a sample suspected of containing a sequence-specific nucleic acid binding protein that will bind to a sequence within the duplex. In all cases, the detection duplex also may contain a moiety that permits capture of the duplex to a solid support or surface. Capture of the duplex can occur before or after mixing with the sample. Use of this capture moiety permits the generation of arrays for detecting multiple binding proteins in a sample, i.e. it permits "multiplexing" of the methods.

After a period of time sufficient to permit binding between the duplex and any proteins in the sample, the duplex is treated with a cleavage reagent. If protein is bound to the duplex, cleavage of the duplex by the cleavage agent is inhibited. Conversely, if no protein is bound, cleavage can proceed. The duplex is labeled in such a fashion that the presence of absence of cleavage can be identified by a change in signal from the label moiety initially present on the duplex. This change in signal then not only indicates the presence of absence of protein binding to the duplex, but the change in magnitude of the signal provides a quantitative measure of the amount of protein binding. The methods can be calibrated using known samples, and the results can also be compared to control reactions.

The cleavage reagent can be non-specific, such as an exonuclease that can cleave one or both strands of the duplex from one terminus, or may be sequence specific, such as a restriction endonuclease that binds to the duplex at a specific site and cleaves at that site (i.e. a Type II restriction endonuclease) or at a defined site some distance from the specific site (i.e. a Type IIs restriction endonuclease). In either case, the presence of a binding protein, such as a transcription factor, bound to the duplex sterically inhibits cleavage of the duplex. Absence of protein binding allows cleavage to occur, and this cleavage liberates the label from the duplex.

In the methods that use a protein recognition element-based mechanism, the proteins in a sample suspected of containing a protein binding protein may be labeled prior to contact with the detection duplex, in which case the binding protein itself functions as the recognition element, or the binding protein is specifically bound to a reagent, such as an antibody or other specific recognition element, before or after binding to the detection duplex. If the binding protein is bound to a reagent prior to mixing with the detection duplex, the duplex itself may be directly labeled to facilitate detection of binding. The detection of the label may be by direct observation or may be facilitated by secondary detection. For example, secondary detection could be achieved by treatment with a cleavage agent that releases a label. Cleavage can only occur if the detection duplex is present, which can itself only occur if the duplex is bound to a specific binding protein.

Definitions

Protein or DNA-Binding Protein

As used herein, "protein" and "DNA-binding protein" refers to any peptide, polypeptide, or peptide-containing substance or complex that can bind specifically to a defined nucleic acid sequence. The DNA-binding protein may be a complex of two or more individual molecules. Such complexes are commonly referred to as "homodimers", "heterodimers" "homotypic complexes" and "heterotypic complexes." Such complexes are composed of any number of individual entities that are held together by covalent bonds or non-covalent interactions. The DNA-binding protein may be natural or synthetic and is not required to be in any particular form. Examples of well-known DNA-binding proteins include AP-1, Jum, Fos, CREB, ATF-1, Myc, Max, NF-kappa B, PPARγ, and Ubx. Nucleic acid-binding proteins of all kinds such as polymerases, proteins of the telomerases complex, gyrases, and splicing proteins, are also included in this definition.

Sample

As used herein, "sample" refers to any material that might contain a DNA-binding protein including but not limited to human and animal tissues, cultured cells, cultured or naturally occurring microorganisms, bodily fluids, blood, serum, and the like. The sample need not contain only the biological material. The sample may also consist of a DNA-binding protein-containing material on or in a physical matrix.

Detection Duplex

As used herein, "detection duplex" refers to a DNA molecule containing a double-stranded region that comprises a protein binding site. The detection duplex may be partially single-stranded and partially double-stranded and may contain gaps and nicks. The detection duplex may be constructed of one or more oligonucleotides and may comprise one or more self-hybridized regions that form hairpin loops. The detection duplex may contain any combination of natural and non-natural nucleotides and may contain non-natural linkages between nucleotides. The detection duplex may comprise one or more detectable labels. The detection duplex may comprise one or more binding moieties. The detection duplex may comprise one or more modifications that affect the stabilization of single-stranded or double-stranded DNA. Such modifications may include inverted 'T' residues, thiolated residues, peptide nucleic acid linkages, chimeras or RNA and DNA, and the like. The detection duplex may be immobilized on a support or may be capable of being immobilized on a support through a binding moiety or through hybridization of a single-stranded portion of the detection duplex to a complementary sequence on the support. The detection duplex may also contain intentional or unintentional mismatches. Examples of detection duplexes are shown in FIG. 1. The skilled artisan will recognize that a wide range of suitable detection duplexes may be used in the present invention and the examples given in FIG. 1 are not meant to be limiting of the present invention.

Capture Tag

As used herein, "capture tag" refers to a sequence in the detection duplex that can be used to capture the duplex onto a support.

Binding Moiety

As used herein, a "binding moiety" is a chemical or biochemical moiety that may be used to attach a substance such as DNA or protein to a solid support. The binding moiety may form a non-covalent bond, a reversible covalent bond, or an irreversible covalent bond between the substance and the solid support. Examples of chemical binding moieties include the aldehyde moiety (CHO) and amino moiety (—NH2) which may be used to chemically bind the substance to the solid support using techniques well known in the art. The skilled artisan will recognize that other suitable binding moieties are known in the art and may be used in the present invention. Examples of biochemical moieties include biotin, IgG and DNA. A substance labeled with biotin will form a strong non-covalent bond with an avidin-coated solid support. IgG will bind to a solid support coated with Protein G, and DNA will bind to a solid support coated with a complementary RNA or DNA sequence. Other such binding interactions suitable for use in the present invention are known in the art.

Detection Reagent

As used herein, a "detection reagent" is a detectable entity that is capable of binding to a second entity to enable detection of the second entity directly or indirectly. Detection reagents may be nucleic acids, proteins, or peptides, or other biomolecules that may or may not comprise a label. Examples of detection reagents include peptides, oligonucleotides, mono and polyclonal antibodies, antibody fragments, lectins, stains, dyes, and the like and chimeric forms of these entities, thereof. Detection reagents that are not directly detectable may comprise a label or may be detected by a secondary detection reagent that comprises a label. For example, antibodies can be detected with labeled Protein G.

Label

As used herein, a "label" is a detectable signal moiety or a reporter. A wide variety of labels or reporters may be used in the present invention, including, for example, radioactive isotopes, fluorescent labels, chemiluminescent labels, bioluminescent labels, and enzyme labels. Labels may be bound directly or indirectly. The labels also may be haptens that can be recognized by secondary reagents such as antibodies, peptides, direct chemical interactions, and other methods that are well known in the art. The label also may be an oligonucleotide or nucleic acid that can be detected by hybridization, polymerization, ligation and/or amplification by methods well known in the art. The label may be used to generate an increase or decrease in a signal readout. The label may also comprise two chromophores bound in close proximity to utilize a phenomenon called fluorescence resonance energy transfer (FRET). When illuminated with light of the appropriate wavelength, one chromophore absorbs a photon and then exists in the excited state. The energy from the excited chromophore is transferred to an acceptor molecule when the chromophore and the acceptor are in close spatial proximity to each other. This energy transfer prevents the excited chromophore from releasing the energy in the form of a photon of light thus quenching the fluorescence of the chromophore. When the acceptor molecule is not sufficiently close in space, the energy transfer does not occur and the excited chromophore may then fluoresce. Pairs of suitable interacting signal moieties are well known in the art. A similar phenomenon known as luminescence resonance energy transfer (LRET) occurs between sensitized lanthanide metals and acceptor dyes and may be used in the present invention. Additionally, micro- or nano-transponders of nanocrystals may be used as labels. Additionally, other labels that can be used to accelerate detection include chemiluminescent labels, immuno-affinity tags such as c-myc, affinity tags such as cellulose binding domain, streptavidin, biotin, streptavidin or any whole or part macromolecule with a matching fit, reporter enzymes with chromogenic, luminescent, fluorescent, or other tracer capabilities.

Support

As used herein, "support" may be any porous or non-porous material or matrix suitable for attaching proteins, peptides, nucleic acids and the like. The proteins, peptides, nucleic acids and the like may be bound covalently or non-covalently to the support by any technique or combination of techniques well known in the art. Supports of the invention may comprise nylon, nitrocellulose, diazonitrocellulose, glass, silicon, polystyrene, polyvinyl chloride, polypropylene, polyethylene, dextran, sepharose, agar, starch, or any other material that allows for the immobilization of biomolecules. The material can be formed in filters, membranes, flat surfaces, tubes, channels, wells, sheets, particles, beads, microspheres, columns, fibers (e.g. optical fibers) and the like. The support may also comprise a multiwell format (such as microtiter plates) such as 12-well, 24-well 48-well, 96-well, 384-well, and 1537-well plates. Particles or beads may be made of glass, latex, a magnetic material (magnetic, paramagnetic, or supermagnetic beads) or other suitable material. One example of a support that may be used in the present invention is a set of color coded microspheres such as those manufactured and sold by Luminex Corporation (Austin, Tex.)

Array

As used herein, the term "array" refers to an orderly arrangement of distinct molecules or substances on a support including, but not limited to, biological molecules such as DNA, RNA, proteins, and the like or chemicals arrayed or immobilized to a support. Arrays of biological molecules such as oligonucleotides, probes, receptors, antibodies, or any entity reactive with targets have become an increasingly important tool in the biotechnology industry and related fields. Arrays comprising a plurality of biological molecules find use in a variety of applications including drug screening, nucleic acid sequencing, mutation analysis, genomic and proteomic applications and the like. Such arrays may be formed on microplates, glass slides, beads, microspheres, microfluidic devices or standard blotting membranes and may be referred to as "arrays", microarrays, or chips. Capture molecules may be bound to the support through covalent or non-covalent interactions. When bound to a planar surface, the capture molecules are bound in an orderly fashion such that the identity of any particular capture molecule can be identified by its position on the array.

Such arrays may be constructed on planar objects such as glass or plastic microscope slides. Arrays may also be constructed on the inside surface of a tube or microplate well or may be constructed inside the channels of a microfluidic device. In general, there is no restriction on the format of the array provided the individual sites to which the capture molecules are bound can be identified. If the support is a set of beads or microspheres, then sets of beads or microspheres coupled to different capture molecules must be distinguishable in some way. In one embodiment, beads from Luminex Corporation (Austin, Tex.) are color-coded by the addition of two different dyes at 10 different concentrations resulting in 100 different color beads. Capture molecules can be bound to specific bead colors and the color of each bead can be identified by flow cytometry. A bead array is prepared by binding specific capture molecules to sets of beads of a specific color, and then mixing different sets of colored beads to create an array. In another embodiment, microparticles from Pharmaseq (Princeton, N.J.) each containing a unique radio frequency tag, can be used to identify specific microparticles.

Other methods can be used to tag individual beads for identification such as nucleic acid and peptide tags. The array may contain anywhere from 2 to 100,000 elements, preferably, between 3 and 5000 elements. In one embodiment, the invention employs a bead array format such as commercially available Luminex LabMAP™ Technology but can be applied to virtually any type or array platform or format. The invention comprises an assay system with the capacity to quantitatively and qualitatively profile activities of up to 100,000 different regulatory proteins in a single reaction vessel, well or tube.

Capture Reagent

In the present invention, a "capture reagent" refers to any molecule that will specifically capture a DNA-binding protein or a detection duplex from a solution containing one or more biological molecules. Examples of capture reagents are poly- and monoclonal antibodies and antibody fragments. Capture reagents may be molecules that bind to haptens or binding moieties. Proteins that have natural affinity for specific DNA-binding proteins and proteins that have been engineered to specifically bind to the DNA-binding proteins are also included in this definition. Capture molecules may also be molecules that bind to another molecule that binds the DNA-binding protein. For example, anti-rabbit IgG may be used to capture a rabbit antibody-protein complex. Similarly, protein G may be used to capture a goat antibody-protein complex. Examples of capture reagents and corresponding binding moieties are given in Table 1.

TABLE 1

Examples of Capture Reagents and the haptens to which they bind

| Hapten/Binding Moiety | Capture Reagent |
| --- | --- |
| Biotin | Avidin, Streptavidin |
| Sialic Acid, carbohydrates, glycoproteins | Lectins such as Concavalin A |
| Digoxigenin | Anti-digoxigenin |
| Fc portion of IgG | Protein A, Protein G, Protein A/G |
| 5-BrdU (5-bromodeoxyuridine) | Anti-BrdU |
| Dinitrophenyl (DNP) | Anti-DNP |
| Fluorescein isothiocyanate (FITC) | Anti-FITC |
| N-2-Acetylaminofluoren (AAF) | Anti-AAF |

TABLE 1-continued

Examples of Capture Reagents and the haptens to which they bind

| Hapten/Binding Moiety | Capture Reagent |
| --- | --- |
| N-2-Acetylamino-7-iodofluoren (AAIF) | Anti-AAIF |
| oligo or poly dA | oligo or poly dT |
| oligo or poly dC | oligo or poly dG |
| phenylboronic acid (PBA) | salicyihydroxamic acid (SHA) |
| Aldehyde and ketone moieties | Hydrazides |
| Sulfhydryl moiety | Maleimides |
| Amino moiety | N-hydroxysuccinimide esters |
| Thiols (glutathione) | Heavy metals ($^{Hg2+}$) |

Capture reagents may also include chemicals or dyes that can bind to DNA, protein, or DNA-protein complexes. Capture reagents also include reagents that recognize specific conformations of biomolecules or may recognize particular modifications. For example, antibodies that react against phosphoserine can be used as capture reagents to capture proteins that contain an exposed phosphoserine residue. Additionally, SH2 domains may be used to capture proteins that contain a particular four amino acid motif that contains phosphotyrosine.

Profile

As used herein, a "profile" is a combination of the measurements of two or more properties of a biological, biochemical, or chemical system. The measurements may be made simultaneously or in sequence. For example, a profile may comprise the concentration of two or more proteins in a sample. Another example of a profile is the phosphorylation state of two or more proteins in a sample. Profiles may comprise qualitative or quantitative measurements and may include subjective as well as objective data.

Sequence-Specific Cleavage Reagent

As used herein, a "sequence-specific cleavage reagent" is a reagent that can cleave DNA at a specific location based upon the recognition of a specific DNA sequence. Examples of sequence-specific cleavage reagents include Type II restriction endonucleases such as EcoR1, Hind III, and BamHI. Sequence-specific cleavage reagents also include the class of Type IIs (or "homing") restriction endonucleases that bind to a specific DNA sequence, and cleave the DNA at a defined distance from the enzyme binding site.

External Cleavage Reagent

As used herein, an "external cleavage reagent" refers to a reagent that initiates the digestion or cleavage of one or more strands of nucleic acid at or near one or more ends of the nucleic acid. The digestion or cleavage proceeds in a single direction relative to the initiation site. External cleavage reagents include the enzymes commonly known as exonucleases. Examples of external cleavage reagents and their properties are shown in FIG. 2.

Probe Capture Sequence

As used herein, "probe capture sequence" refers to a sequence of DNA that can be used to capture a labeled or unlabeled oligonucleotide or nucleic acid probe. The sequence may be single-stranded or double-stranded. The probe capture sequence may be used to capture detection duplexes or DNA-protein complexes.

Signal Amplification

As used herein "signal amplification" refers to any method used to increase the signal of a biological assay beyond the signal that can be achieved with a "one-label" detection strategy. Signal amplification may be based on an enzyme catalyzed reporter deposition such as tyramide signal amplification or may be based on enzyme amplification. Alternatively, strategies that increase the number of labels may be used. Such strategies include the binding of dendrimers, branched polymers, and long linear polymers that contain multiple binding sites for a secondary detectable reagent. Examples of these strategies include, without limitation, oligonucleotide dendrimers, branched DNA, and Hybrid Capture. Other amplification strategies are known in the art and may be used in the context of the present invention. For example, nucleic acid amplification methods such as polymerase chain reaction and rolling circle amplification also may be used to amplify the signal obtained. Although many of these strategies initially were designed to increase the sensitivity of detecting nucleic acids, they can be readily adapted to detection of other molecules simply by attaching an appropriate nucleic acid molecule to a detection reagent such as an antibody, peptide, avidin, or streptavidin. In the present invention, any method of signal amplification may be used to increase the signal generated by the assay.

The present invention therefore provides compositions and methods for detecting and measuring DNA-binding proteins. In addition, the invention provides compositions and methods for the simultaneous or near-simultaneous detection of multiple DNA-binding proteins in a multiplex or array format, and also provides compositions and methods for generating profiles of DNA binding activity by proteins, specifically, transcription factors. More specifically, the invention provides compositions and methods for detecting and measuring multiple protein-DNA binding events in a single sample in a high-throughput format.

In one embodiment, the invention provides a method for detecting protein binding to a detection duplex, in which binding of the protein to the detection duplex inhibits cleavage of the duplex by a site-specific cleavage reagent and thereby increases or diminishes a signal.

Figure 3:
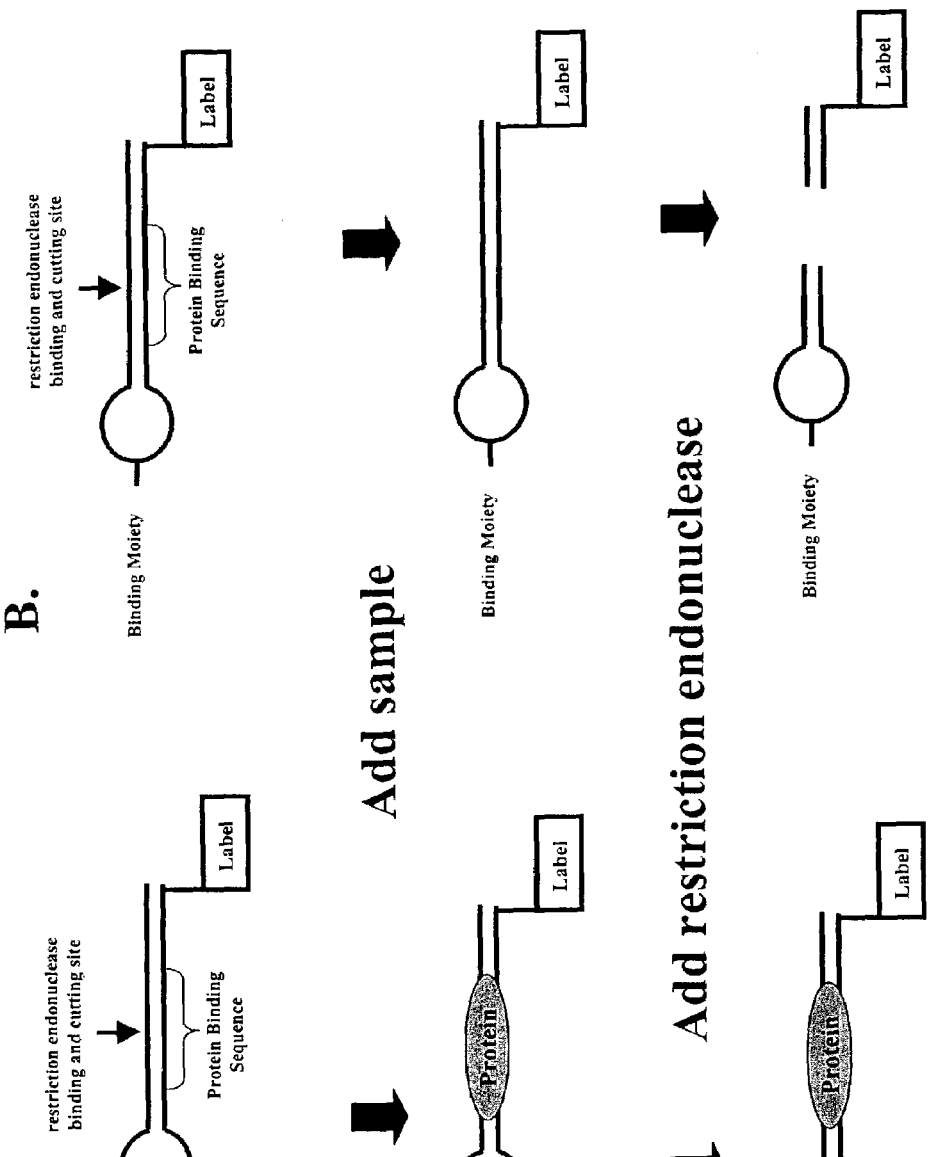
FIG. 3 illustrates the detection of protein binding by protection from cleavage by site-specific cleavage reagents, specifically, type II restriction endonucleases. In this embodiment, the detection duplex contains a cleavage site for a restriction endonuclease in the protein binding sequence. Samples that may contain DNA-binding proteins are mixed with the duplexes, and DNA-binding proteins, if present, bind to the protein binding sequence. Subsequently, a restriction endonuclease is added. If protein has bound to the protein binding sequence, then the restriction endonuclease cannot cleave the double-stranded DNA and the label will be detected (FIG. 3A). If no protein has bound to the protein-binding sequence, then the restriction endonuclease will cleave the DNA and release the detectable label which will be washed away and will not be detected (FIG. 3B).

In this mode of the invention, the detection duplex comprises a DNA sequence that is recognized by a site-specific cleavage reagent such that the site-specific cleavage reagent will cleave the detection duplex when no protein has bound to the protein-binding site. However, if protein has bound to the protein-binding site of the detection duplex, the cleavage of the detection duplex will be inhibited and thereby increase or decrease a signal. Type II restriction enzymes may be used in this mode of the invention when the protein binding site in the detection duplex comprises a known site for a type II restriction enzyme, or is sufficiently close in space to the restriction enzyme site that binding of a specific binding protein to the protein binding site that restriction enzyme binding to the enzyme recognition site is inhibited or prevented. For example, a detection duplex comprising a binding moiety, a label, and a protein binding site between the binding moiety and the label wherein the protein binding site comprises a restriction endonuclease cleavage site may be used. The detection duplex is contacted with the sample and DNA-binding proteins, if present, bind to the detection duplex. A site-specific cleavage reagent such as a type II restriction endonuclease is added. If protein has bound to the protein-binding site, then the detection duplex remains intact. If no protein has bound to the detection duplex, then the detection duplex is cleaved, thus separating the binding moiety from the label and preventing the label from being detected. An example of this embodiment of the invention is illustrated in FIG. 3.

Figure 4:
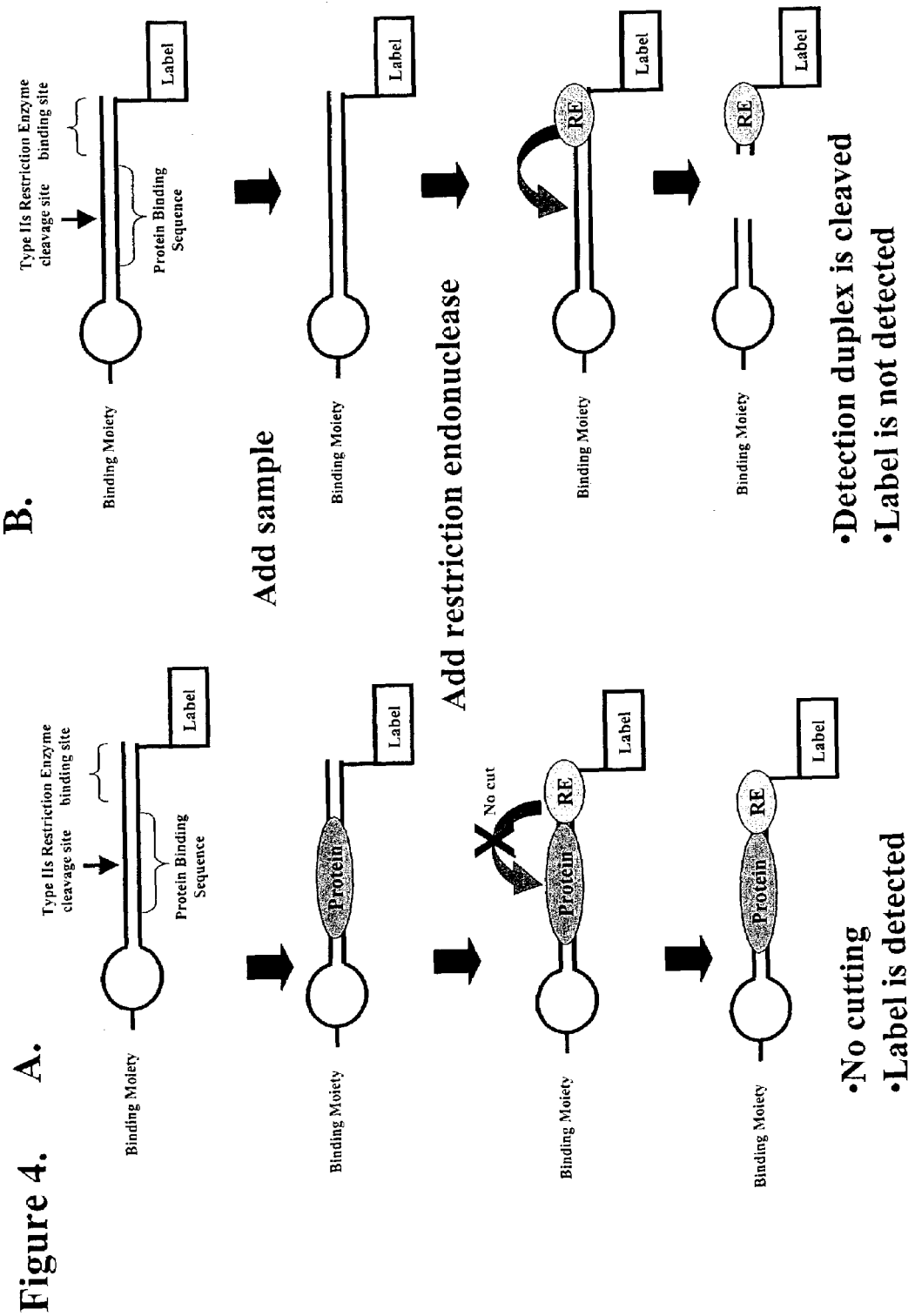
FIG. 4. This figure illustrates the detection of protein binding by protection from cleavage by site-specific cleavage reagents, specifically type IIs restriction endonucleases that cleave DNA at a defined distance from the enzyme binding site. In this embodiment, the detection duplexes contain a binding site for homing restriction endonucleases outside of the protein binding sequence. Samples that may contain DNA-binding proteins are mixed with the duplexes, and DNA-binding proteins, if present, bind to the protein-binding sequence. Subsequently, a type IIs restriction endonuclease is added to the reaction. The type IIs restriction endonuclease binds to its specific binding site in the duplex and attempts to cleave the DNA strand in the protein binding sequence. If protein has bound to the protein binding sequence, then the homing restriction endonuclease will not be able to cleave the double-stranded DNA and the label will be detected (FIG. 4A). If no protein has bound to the protein-binding sequence, then the type IIs restriction endonuclease will cleave the DNA and will release the detectable label which can be washed away and will not be detected (FIG. 4B).

Another type of site-specific cleavage reagent may be used in this mode of the invention. Type IIs restriction endonucleases recognize and bind to a specific DNA sequence but cleave the DNA at a defined region away from the enzyme binding site. Assays utilizing these enzymes are advantageous because the protein binding site need not comprise a recognition sequence for the site specific cleavage reagent. Rather, the binding site for the site-specific cleavage reagent can be designed into the detection duplex. In this example, a detection duplex comprising a binding moiety, a label, a protein binding site, and a binding site for a site-specific cleaveage reagent such that the site specific-cleavage reagent, when bound to the detection duplex, cleaves the duplex in or near the protein binding site. The detection duplex is contacted with the sample and DNA-binding proteins, if present, bind to the detection duplex. A site-specific cleavage reagent such as a type II restriction endonuclease is added. If protein has bound to the protein-binding site, then the detection duplex remains intact. If no protein has bound to the detection duplex, then the detection duplex is cleaved, thus separating the binding moiety from the label and preventing the label from being detected. An example of this embodiment of the invention is illustrated in FIG. 4. The duplex may be captured onto a support to facilitate the detection of the label.

Figure 5:
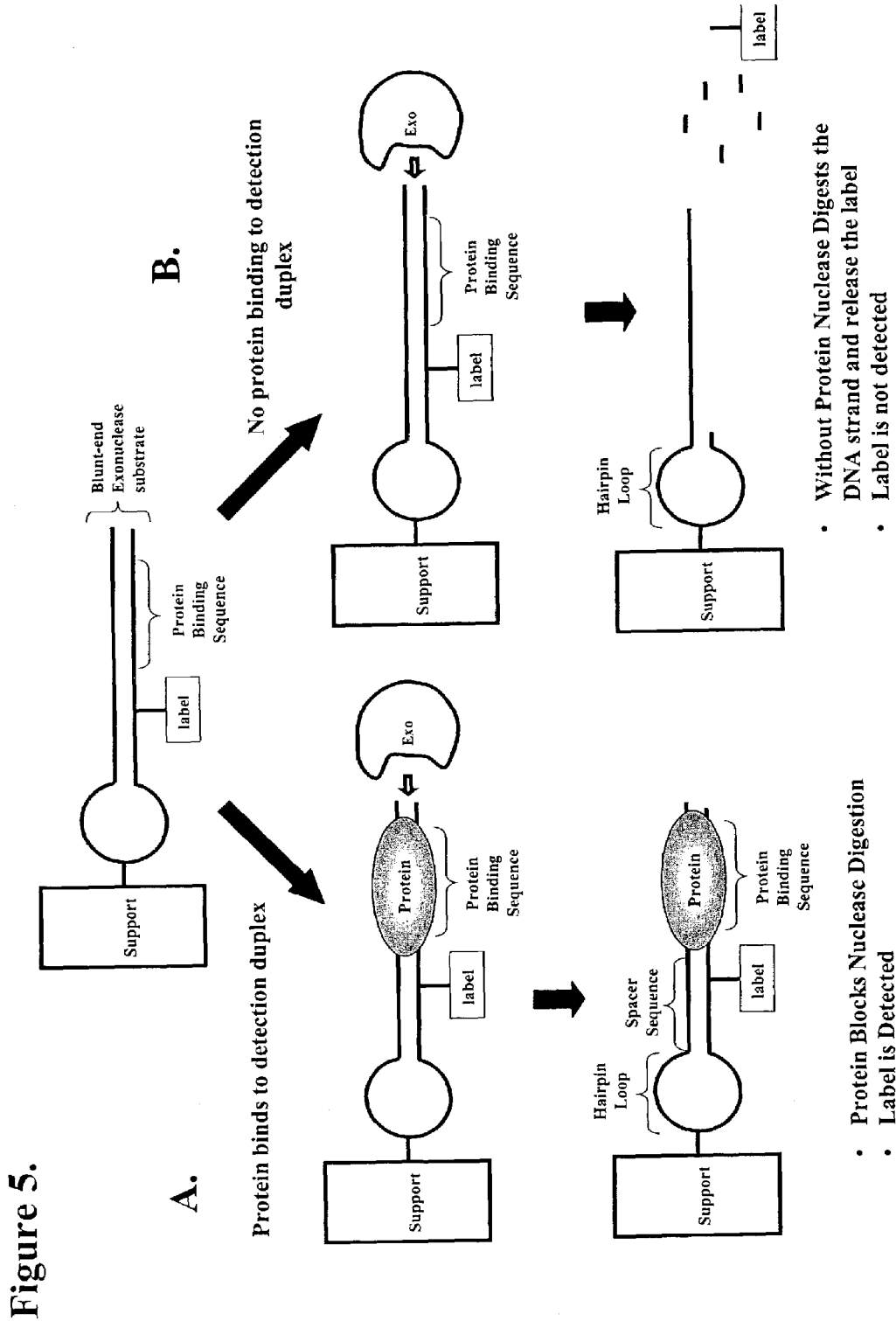
FIG. 5. This figure illustrates the detection of protein binding to DNA by protection of the detection duplex from digestion by external cleavage reagents. In this example, the detection duplex is bound to a support. The blunt end of the double-stranded DNA sequence is a substrate for blunt-end specific exonucleases such as T7 exonuclease and exonuclease III. A detectable label is attached to the detection duplex between the support and the protein binding sequence. Samples that may contain DNA-binding proteins are mixed with the duplexes and DNA-binding proteins, if present, bind to the protein-binding sequence. Subsequently, a blunt-end exonuclease is added. If no protein has bound to the protein-binding sequence, then the exonuclease is free to digest the detection duplex in the direction of the support. In this process, the detectable label is released and will not be detected (FIG. 5B). If protein has bound to the protein binding sequence, then the exonuclease will not be able to digest the detection duplex past the binding site. Accordingly, the label will remain attached to the detection duplex and the support and will be detectabed (FIG. 5A).

In another embodiment, the invention provides a method for detecting protein binding to a detection duplex, in which binding of the protein to the detection duplex inhibits the cleavage of the duplex by an external cleavage reagent and thereby increases or diminishes a signal. The external cleavage reagent may cleave one or both strands of the detection duplex beginning at one or more ends of the DNA strand in the duplex. In one form of this embodiment, the detection duplex is first immobilized on a support. The sample is contacted with the detection duplex on the support and protein is allowed to bind to the detection duplex. Subsequently, an external cleavage reagent is brought into contact with the detection duplex on the support. If protein has bound to the detection duplex, then the external cleavage reagent will not be able to fully digest the detection duplex because it will be protected by the presence of the protein. If no protein is bound to the detection duplex, then the external cleavage reagent will digest one or both strands of the detection duplex and will release the label into medium where it can be washed away. If protein has bound to the detection duplex, then the label will remain bound to the support and will be detected. An example of this embodiment of the invention is illustrated in FIG. 5.

Figure 6:
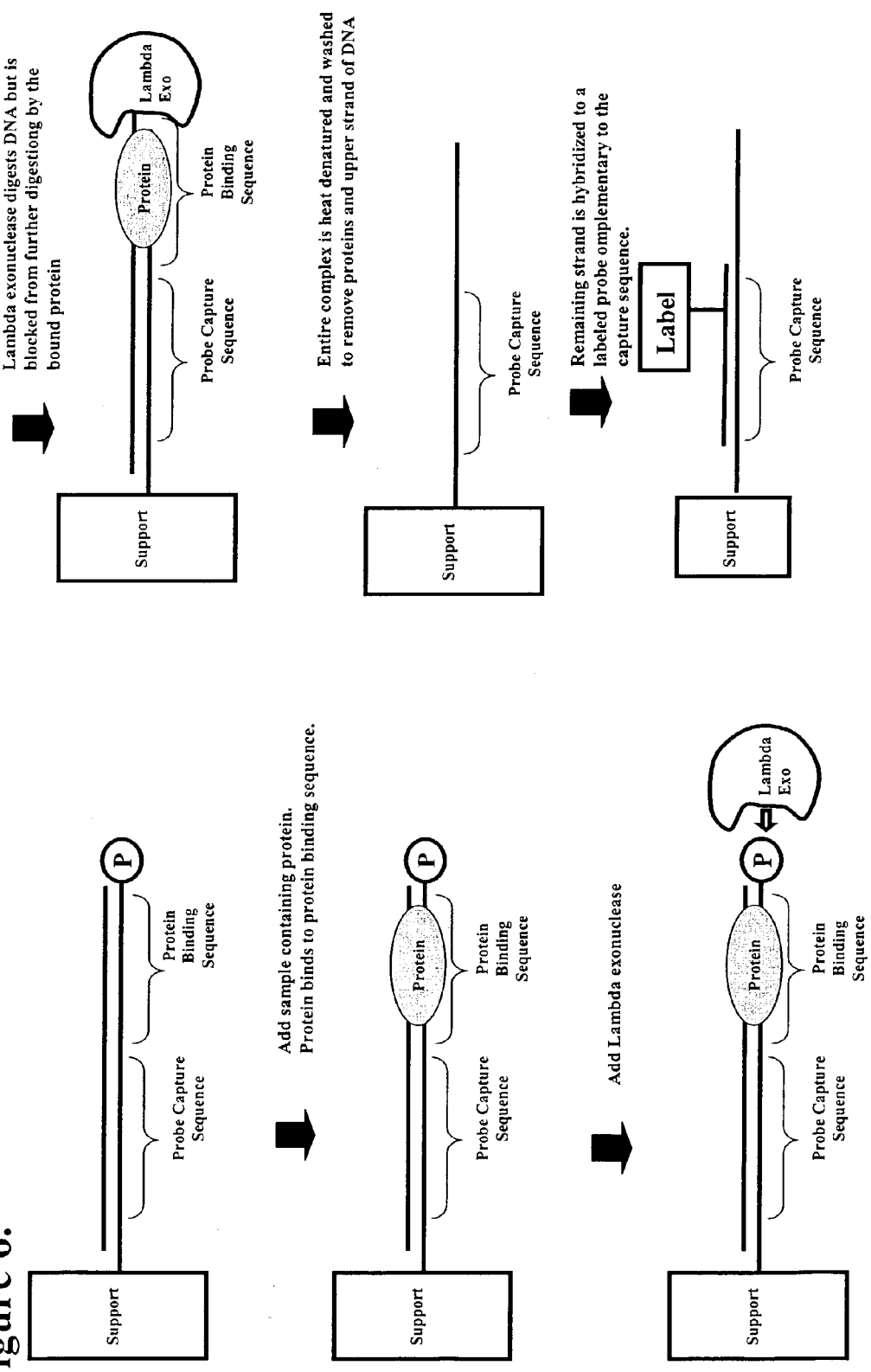
FIGS. 6 and 7 illustrate the detection of protein binding to a detection duplex through the protection of a probe capture sequence and subsequent detection of the probe capture sequence through hybridization with a detectable probe. In this example, the detection duplex is bound to a support. The first strand of the DNA is covalently bound to the support on the 3' end and is labeled with phosphate on the 5' end. The second DNA strand is bound to the first DNA strand through hybridization. The detection duplex contains a protein binding sequence and a probe capture sequence wherein the probe capture sequence is between the support and the protein binding sequence. The probe capture sequence is designed to be complementary to a labeled oligonucleotide or nucleic acid probe. The DNA is mixed with a sample, and proteins, if present, bind to the protein binding sequence. Subsequently, lambda exonuclease is added to the reaction. Lambda exonuclease specifically digests only DNA strands from the 5' end that are phosphorylated. If protein has bound to the protein binding sequence, then the DNA strand will be protected from lambda exonuclease digestion (FIG. 6). Next, the reaction mix is heat denatured and washed. The heat denaturation and washing will inactivate and remove the lambda exonuclease, separate the protein from the DNA binding sequence, and separate the strands of DNA all of which are washed away. The first DNA strand which contains the probe capture sequence remains bound to the support. A labeled oligonucleotide or nucleic acid is hybridized to this probe sequence to detect the presence of this strand. Alternatively, the protein binding sequence can also be used as the probe capture sequence. However, such a format would require a different labeled oligonucleotide for each protein capture sequence in a multiplex format whereas the arrangement with a separate probe capture sequence can be designed such that every probe capture sequence is the same while all of the protein binding sequences can be different.
Figure 7:
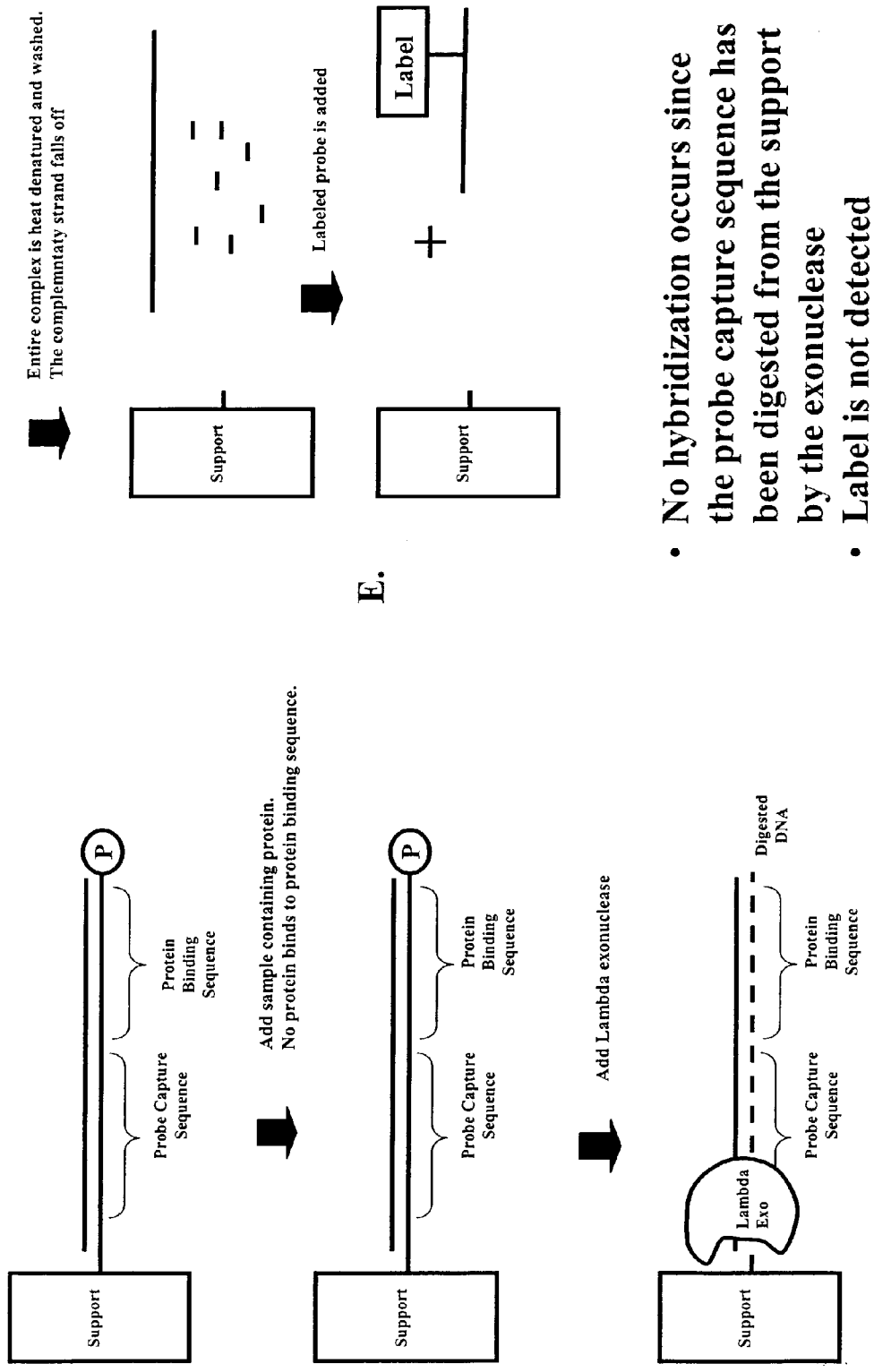

Another example of this embodiment is illustrated in FIGS. 6 and 7. In this example, the immobilized detection duplex comprises a probe capture sequence and a protein binding sequence and a phosphate moiety on the 5' end of the immobilized or immobilizable strand. The detection duplex may be immobilized on a support or may be captured onto a support at other steps as may be advantageous. The capture sequence and the protein binding sequence may be the same or may be different. In an array format it will be advantageous for the probe capture sequence and the protein binding sequence to be different so that the same detection reagent can be used with many different detection duplexes.

In this example, the detection duplex is contacted with the sample that may contain DNA-binding proteins. If present, the proteins bind to the protein-binding site in the detection duplex. The detection duplex is then contacted with lambda exonuclease, an external cleavage reagent, that digests the 5' phosphorylated DNA strand in a 5' to 3' direction. If protein has bound to the detection duplex, then the enzyme will be prevented from cleaving the phosphorylated strand of the detection duplex. If no protein has bound, then the 5' phosphorylated strand of the detection duplex will be completely digested. The detection duplex is then heat denatured and washed to inactivate the external cleavage reagent, separate the strands of the detection duplex, and remove the cleavage products. If the detection duplex was protected by protein binding, then the strand containing the probe capture sequence remains bound to the support. If the duplex was not protected because no protein bound to the detection duplex and inhibited the digestion, then the strand containing the probe capture sequence will no longer be on the support. A labeled oligonucleotide or nucleic acid probe is then added and allowed to hybridize to the probe capture sequence, if present. The presence of signal indicates that the detection duplex was protected by bound protein (FIG. 6). The absence of signal indicates that the strand was digested by the external cleavage reagent and was not protected by protein binding (FIG. 7).

A further embodiment of the invention provides a method for detecting protein binding to a detection duplex in which the proteins in a sample are labeled prior to or subsequent to binding to a detection duplex. After washing, proteins that have bound to the detection duplex are detected by the presence of the label bound to the detection duplex. Proteins in the sample are labeled by methods commonly used in the art including active esters such as N-hydroxysuccinimide esters of biotin, N-hydroxysuccinimide esters of fluorescent dyes such as Cy3 and Cy5, sulfhydryl-reactive labels and other methods commonly used in the art. In one example of this embodiment, a sample is labeled with an amine reactive dye such as the N-hydroxysuccinimide ester of the fluorescent dye Cy3 (Amersham Biosciences). The process will label essentially all, or nearly all of the proteins in the sample. The labeled sample will then be contacted with a detection duplex. The detection duplex may be immobilized on a support of may be in solution. An incubation period ensues to allow proteins to bind to the protein binding site in the detection duplex. If the detection duplex is in solution, it is now captured onto a support, and the unbound molecules are washed away. Proteins bound to the detection duplex are detected by the label. An example of this embodiment of the invention is illustrated in FIG. 8.

In another variation of this embodiment, two or more samples are labeled separately with different labels and then mixed. This mixed sample is then contacted with the detection duplex. An incubation period ensues to allow time for the labeled proteins to bind to the detection duplex. If the detection duplex is in solution, it is now captured onto a support, and the unbound molecules are washed away. Proteins bound to the detection duplex are detected by detection of the labels. Since two or more samples were labeled with different labels, each label is detected and measured independently and the results can be expressed as a differential analysis of DNA-binding proteins in the two samples in a similar manner to the way RNA molecules are differentially labeled and measured on DNA microarrays (27).

Yet another embodiment provides a method for detecting protein binding to a detection duplex in which the proteins in a sample are bound to a detection duplex, after which excess proteins are washed away and bound proteins are subsequently detected with a detection reagent. The detection duplex may be first captured onto a support or may be captured onto the support after other steps as may be advantageous. The order of contacting the duplex, sample and detection reagent may be carried out in any order. In one example of this embodiment, an immobilized detection duplex is contacted with a sample that may contain DNA-binding proteins. The immobilized detection duplex is incubated with the sample to allow the proteins to bind to the detection duplex. Unbound substances are washed away and the bound proteins are detected with a detection reagent. This example is illustrated in FIG. 10. The proteins may be detected with specific antibodies that detect only a single protein or may be detected with antibodies that detect classes of proteins or particular protein motifs. For example, many DNA-binding proteins contain phosphorylated tyrosine, threonine, or serine residues and proteins may be detected with anti-phosphotyrosine, anti-phosphoserine, and anti-phosphothreonine antibodies. Proteins may also be detected with other proteins that binds to certain motifs. For example, DNA-binding proteins may be detected with a class of proteins called SH2 domains. SH2 domains bind to a 4 amino acid motif that includes phosphotyrosine. Bound proteins may also be detected with a chemical or biochemical stain.

A further embodiment of the invention provides a method for detecting protein binding to a detection duplex in which the protein is first bound to a labeled detection duplex, after which the protein-detection duplex complex is captured onto a support with a capture reagent and detected. Alternatively, the capture reagent, protein, and labeled detection duplex may be first contacted and subsequently captured onto a support. In general, the addition of capture reagent, sample and labeled detection duplex and the capture onto a support may be carried out in any order. In one example of this embodiment, the capture reagent is immobilized onto a support. The labeled detection duplex is contacted with the sample that may contain DNA-binding proteins. The sample is incubated with the detection duplex to allow proteins, if any, to bind to the detection duplex. After incubation, the mixture is contacted with an immobilized capture reagent that captures the protein-detection duplex complex onto the support and the label on the detection duplex is detected. This example is illustrated in FIG. 11. If no protein bound to the detection duplex, then the protein still may be captured by the capture reagent, but no label will be detected since the label is attached to the detection duplex. In this example, the capture reagent could be an antibody to a specific DNA-binding protein that has been immobilized on the support.

In another example of this embodiment, illustrated in FIG. 12, the labeled detection duplex is contacted with the sample that may contain DNA-binding proteins. The sample is incubated with the detection duplex to allow proteins, if any, to bind to the detection duplex. After incubation, the mixture is contacted with a first capture reagent that binds to the protein-detection duplex complex. The first capture reagent-protein-detection duplex complex is then captured onto a support through a second capture reagent and the label on the detection duplex is detected. In this example, the first capture reagent could be an antibody specific for a DNA-binding protein and the second capture reagent on the support could be a molecule such as Protein A or Protein G that could bind the first antibody capture reagent.

The embodiments of the invention already described are readily adaptable for use in an array format. In particular, the invention provides for a method of detecting DNA-binding proteins comprising two or more detection duplexes immobilized on a support. In another embodiment, the invention provides a method of detecting a plurality of DNA binding proteins using two or more detection duplexes. The duplexes are mixed with the sample in solution and subsequently are captured onto a support in an array format. For example, detection duplexes containing unique single-stranded regions can be bound to a support that comprises an array of oligonucleotides that are complementary to the single-stranded regions of the detection duplexes. Additionally, detection duplexes may be captured onto a support in an array format through a binding moiety either prior to or subsequent to contact with the sample. The array may also comprise an array of antibodies or other capture reagents that can be used to capture DNA-binding protein-detection duplex complexes.

The invention described herein is well suited to application on a flow cytometric bead array with multiplex capability such as the LabMap system developed by Luminex Corporation (28). To make a bead array, polystyrene microspheres are internally dyed with precise ratios of two spectrally distinct fluorescent dyes. Each bead is dyed with one of 10 different concentrations of each fluorochrome resulting in a bead array consisting of 100 spectrally distinct microsphere sets. Each microsphere set can be distinguished by its spectral address (the ratio of two dye colors) and they can be combined in a single test allowing up to 100 different analytes to be measured simultaneously in a single reaction vessel. Substances such as proteins, peptides, nucleic acids, and the like can be coupled to the microspheres using standard chemisty that is will known in the art. A third fluorescent dye is coupled to a reporter molecule quantifies the biomolecular interaction that has occurred at the microsphere surface. Microspheres are interrogated individually in a rapidly flowing fluid stream as they pass by two separate lasers. High speed digital signal processing classifies the microsphere based on its spectral address and quantifies the reporter signal on the surface of the bead. Washing to remove unbound reporter is usually not necessarily, thus making the assay essentially homogeneous. Thousands of microspheres are interrogated per second resulting in an analysis system capable of analyzing and reporting up to 100 different reactions in a single reaction vessel in a few seconds. The embodiments of the present invention can be easily adapted to a bead array format by binding detection duplexes, oligonucleotides, or capture reagents to beads. Detection duplexes may be immobilized on the beads or may be captured onto the beads after contact with the sample. Antibodies or other capture reagents may be immobilized onto the beads or complexes may be captured onto the beads after contact with the sample.

The methods of the present invention may easily be adapted for use in conjunction with signal amplification methods that are used to increase the sensitivity of detection. Enzyme amplification, rolling circle amplification, ligase chain reaction, and other methods that can amplify a detectable signal are included in the scope of this invention.

Methods of the present invention may be used in the detection, screening, and diagnosis of various diseases, disorders, or conditions in biological samples. The methods of the invention may also be used to for monitoring the progression of a disease or treatment. Methods of the present invention may also be used to screen compounds or biological molecules that may affect or alter the activity or the amount of DNA-binding proteins in a samples. The present invention may also be used to determine the effect of genetic variation on the binding ability of DNA-binding proteins. For example, the invention could be used to simultaneously measure the affinity of a single or multiple DNA-binding proteins to a large number of different protein binding sequences.

The present invention provides methods that can be used to elucidate and understand cellular networks and cellular signaling pathways. Profiles of DNA-binding proteins generated by the methods and compositions of this invention may be combined with software that analyzes the data and the profiles generated. Such software may include features such as pattern recognition and pattern discovery algorithms, unsupervised or supervised hierarchical clustering, and the like that will facilitate discovery of new bio-markers, diagnosis and staging of diseases, and can predict the effects of potential new drugs. The methods of the present invention may also be used in conjunction with software that correlates proteins and protein binding sequences with their functional and biological characteristics. Such characteristics may include structural, regulatory or enzymatic functions of the proteins detected, the biological 'objectives' to which the proteins contribute, the functional relationship of the detected protein to one or more other proteins or genes, the functional relationship of protein-binding sequences to other proteins or nucleic acid sequences, the relationship of detected proteins to major biological processes and biochemical functions.

Combinations of the methods described in the present invention with computer software and computer and laboratory hardware and are encompassed by this invention.

EXAMPLES

Example 1

Bead Coupling.

Oligonucleotides were coupled to beads using standard EDC carboxylate coupling chemistry. Briefly, beads are suspended in MES buffer pH 4.7 and oligonucleotides are added to a final concentration of 2 uM. Fresh EDC is added to provide a final concentration of 1–2 mg/ml and is reacted with the bead suspension for 30 minutes while rotating in the dark. A similar concentration of fresh EDC is again added to the bead suspension and reacted for and additional 2 hours while rotating in the dark. Coupled beads are washed once with 50 mM Tris pH 7.5, 100 mM NaCl, 0.05% tween-20, once with 0.2% SDS in PBS, twice with PBS pH 7.5 containing 0.02% Tween-20, once with PBS pH 7.5 and resuspended in PBS pH 7.5 to a final concentration of 1000–2000 beads/microliter.

Example 2

Detection of Protein Binding to Detection Duplexes with Detection Reagents Using a Capture Tag.

Oligonucleotide Annealing:

Detection duplexes were assembled from the oligonucleotide PO4Kbfor (P04-AGTTGAGGGGATCCCCAGGAGCGGCT-TATCGGTCTATTC-AACTCCCCTAGGGG) (SEQ ID NO: 1) that carries a tag sequence, NF-kB binding site and 5 prime phosphate group, and the complement oligonucleotide KBrev (TCCTGGGGATCCCCTCAACT) (SEQ ID NO: 2) devoid of tag sequence.

P04 Kbfor and KBrev were annealed by first diluting 100 uM oligonucleotide stocks into annealing buffer (40 mM Tris pH 7.5, 100 mM NaCl, and 1 mM EDTA), to give a ratio of 20 nM P04 Kbfor: 1 uM KBrev. 100 ul of the oligonucleotide mix was then heated to 95° C. for 1 minute, and cooled linearly to room temperature over a period of 45 minutes. 1 ul of the annealed mixture containing detection duplexes displaying a single stranded tag sequence was added to 19 ul of transcription factor binding buffer (10 mM tris pH 7.5, 50 mM NaCl, 2 mM KCl, 2 mM MgCl2) containing 250 ng poly dI-dC, and 0.5% bovine serum albumin (fraction V) and incubated with varying amounts of NF-kB P50 protein for 15 minutes at room temperature. 1800 beads suspended in 25 ul of transcription factor binding buffer containing 0.35% BSA was added to appropriate reactions and incubated 30 minutes at room temperature. Following the hybridization of DNA binding protein-detection duplex complexes to bead surfaces, 25 ul of transcription factor binding buffer containing (0.1 ug) of NF-kB P50 specific primary antibody (Santa Cruz Biotechnolgy Cat #SC-114) was added to the detection duplex-sample-bead mix and incubated for 20 minutes at room temperature in the dark while shaking. Using a filterplate (Millipore MABV1250) and vacuum manifold, beads were washed 1 time with 100 ul of transcription factor binding buffer containing 0.35% BSA. 50 ul of a 1:500 dilution of Phycoerythrin-labeled anti-rabbit secondary anti body (Sigma Cat.#P9537) was added to each assay and following a 30 minute incubation while shaking in the dark at room temp. 25 ul of each assay were read using the Luminex 100 instrumentation. Data from this experiment is shown in FIG. 12 and the signal obtained shows a dose dependent response to the amount of DNA-binding protein added to the detection duplex.

Example 3

Detection of Protein Binding to DNA with a Capture Reagent

Two micrograms of capture reagent (Santa Cruz Biotechnologies NFKb P65 antibody Cat#SC-372) is incubated with bead supports that are covalent coupled to recombinant Protein G (Upstate Biotechnology). This incubation is carried out while shaking for 2 hours at room temperature in the absence of light. Beads are then washed with 3×200ul volumes of transcription factor buffer to remove antibodies not bound the protein G bead surface. 200 fmoles of biotin-HPNFKB65 hairpin detection duplex

```
biotin-TATCCAAGGGGACTTTCCCCTG
                               G
     3' ATAGGTTCCCCTGAAAGGGGAC
         (SEQ ID NO: 3)
``` is incubated with 2ug of nuclear extracts obtained from control and TNF alpha stimulated HeLa cells for 10 minutes at room temperature in 20 ul of transcription factor binding buffer (10 mM tris pH 7.5, 50 mM NaCl, 2 mM KCl, 2 mM MgCl2) containing 1ug poly dI-dC, and 0.5% bovine serum albumin (fraction V). Following the incubation of samples with detection duplexes, 25 ul of transcription factor binding buffer containing 1000 protein-G beads bound to capture reagent are added to each assay and incubated for 30 minutes at room temperature. Beads are then washed with 2×200 ul volumes of transcription factor binding buffer to remove hairpin oligonucleotides not captured on bead surfaces. Each assay is then resuspended in 100 ul of streptavidin-phycoerythrin (SA-PE) conjugate (2 ug/ml in transcription factor binding buffer), incubated for 10 minutes at room temperature and analyzed using the Luminex 100 instrumentation.

TNF Stimulated extracts contain active NF-kB P65 protein that forms a complex with hairpin oligonucleotides used for detection. The NF-KB P65-hairpin oligonucleotides are captured by the anti-P65 antibodies immobilized on bead surfaces and NF-KB P65-biotinylated-DNA complexes associated with bead surfaces are detected using SA-PE.

Example 4

Detection of Protein Binding to DNA with Inhibition of Site-Specific Cleavage

In this example, Class II restriction endonucleases are used with detection cuplexes comprising hairpin oligonucleotides coupled to beads. Class II restriction enzymes cleave double stranded DNA at the same site where they recognize and bind to DNA.

Hairpin oligonucleotides (KBREHP biotin-TCCAAGG GGATTCCCCAGTG (SEQ ID NO: 4)-amino C-6-TACTG GGGAATCCCCTTGGA) (SEQ ID NO: 5) that present overlapping transcription factor (NE-kB) and restriction enzyme (EcoRI) binding sites are coupled to bead surfaces through amino-C6 using standard EDC chemistry as described previously. Approximately 1000 of the coupled beads are used per 25 ul assay. KBREHP coupled beads are incubated for 10 minutes at room temperature with 2 ug of nuclear extracts (obtained from control and TNF treated HeLa cells) in a 25 ul volume of transcription factor binding buffer (10 mM tins pH 7.5, 50 mM NaCI, 2 mM KGI, 2 mM MgCl2) containing 100 ng poly dI-dC, and 0.35% bovine serum albumin (fraction V). Following binding, reactions were brought to 50 ul with transcription factor binding buffer and supplemented with 1M MgCl2 to provide a final concentration of 10 mM MgCl2. Samples are then incubated with 10 u of restriction endonuclease EcoRI for 10 minutes at 37 degrees. 50 ul of 2 ug/ml Streptavidin-phycoeythrin (SA-PE) is added to each reaction and incubated for 10 minutes at room temperature prior to analysis using the Luminex 100 instrumentation. Active NF-kB P50 binds to DNA and protects from digestion with EcoRI endonuclease. NF-kB is quantified as a measure of signal retained on bead surfaces.

Example 5

Detection of Protein Binding to DNA with Inhibition of Site-Specific Cleavage by Class IIs Restriction Endonucleases.

Detection duplexes were assembled by hybridizing oligonucleotides designated FOR (biotin-AAGGAT-GAGCGGGGGATCCCAATAGGCGGC-TGCTTATCG-GTCTAT) (SEQ ID NO: 6) that comprise an Nf-KB binding site, Fok1 binding site and tag sequence to oligonucleotides designated bREV (CTATTGGGATCCCCGCTCATCCTT) (SEQ ID NO: 7) that is complementary to the FOR oligonucleotide but is devoid of complementary tag sequence.

Hybridization of oligonucleotide pairs was accomplished as follows: bREV and FOR were diluted to 1 uM and 40 nM respectively in buffer containing 40 mM Tris pH 7.5, 100 mM NaCl, and 1 mM EDTA. Oligonucleotides then were heated to 95° C. for 1 minute and allowed to cool to room temperature over a period of 45 minutes.

Binding of transcription factors was carried out by incubating 1 ul of hybridized oligonucleotide with recombinant NF-kB P50 transcription factor (Promega Cat#) in a total volume of 15 ul binding buffer (10 mM tris pH 7.5, 50 mM NaCl, 2 mM KCl, 2 mM MgCl2) containing 100 ng poly dI-dC, and 0.35% bovine serum albumin (fraction V). Following a 10 minute incubation at room temperature, each assay was mixed with 15 ul of binding buffer supplemented to 20 mM MgCl2 and containing 1 ul of FokI (4 units) or 1 ul of FokI storage buffer and incubated for and additional 10 minutes at 37 degrees. 30 ul of transcription factor binding buffer containing Luminex beads (1000 beads) coupled with single stranded capture oligonucleotide (ATAGAC-CGATAAGCAGCCGC) (SEQ ID NO: 8) was added to each assay and incubated for 30 minutes to immobilize the digested and undigested detection duplexes on bead surfaces. To visualize biotinylated oligonucleotides associated with bead surfaces, 60 ul of 2 ug/ml Streptavidin-phycoeythrin (SA-PE) was added to each reaction 10 minutes prior to analysis using the Luminex 100 instrumentation. Active NF-kB P50 binds to DNA and protects from digestion by FokI type IIs restriction endonuclease. NF-kB is quantified as a measure of signal retained.

Example 6

Detection of Protein Binding to DNA by Inhibition of External Cleavage Reagent

Lambda exonuclease is highly specific for double stranded DNA carrying a 5 prime phosphate and has greatly reduced activity on DNA that is not phosphorylated. Lambda exonuclease digestion of DNA occurs in the 5' to 3' direction.

Oligonucleotide PO4Kbfor (P04-AGTTGAGGGGATCCCCAGGAGCGGCT-TATCGGTCTA-TTCAACTCCCCTAGGGG) (SEQ ID NO: 9) carrying tag sequence, NF-kB binding site and 5 prime phosphate group, was annealed to the biotinylated complement oligonucleotide biotinKBrev (TCCTGGG-GATCCCCTCAACT-biotin) (SEQ ID NO: 10) devoid of capture tag sequence.

Annealing was carried out by first diluting 100 uM oligonucleotide stocks into annealing buffer (40 mM Tris pH 7.5, 100 mM NaCl, and 1 mM EDTA), to give a ratio of 400 nM P04 Kbfor: 10 uM biotinKBrev. The oligonucleotide mix was then heated to 95° C. for 1 minute, and cooled to room temperature over a period of 45 minutes of to form a double stranded pair displaying a single stranded tag sequence. Approximately 50,000 beads coupled to tag capture sequence were hybridized with 50 ul of annealed oligonucleotide for 1 hour at room temperature. Beads were then washed to remove unhybridized oligonucleotide and resuspended in transcription factor binding buffer.

DNA binding to P50 transcription factor was carried out by incubating 0.5 gel shift units of recombinant P50 (Promega cat#E3770) (defined as the amount of P50 required to shift 190 fmoles of double stranded NF-kb binding oligonucleotide using conventional gel shift assay-promega) with 1000 hybridized beads in a 20 ul volume of transcription factor binding buffer (10 mM tris pH 7.5, 50 mM NaCl, 2 mM KCl, 2 mM MgCl2) containing 100 ng poly dI-dC, and 0.35% bovine serum albumin (fraction V). Following a 10 minute incubation at room temperature, 20 ul of transcription factor binding buffer supplemented to 3 mM $MgCl_2$ containing 3 units of lambda exonuclease or an equivalent of lambda exonuclease storage buffer was added to appropriate reactions and incubated for 15 minutes at 37 degrees. Following enzyme digestion, 40 ul of 4 ug/ml streptavidin-PE conjugate in PBS pH=7.5 added to samples 10 minutes prior to analysis using Luminex 100 instrumentation. Results of this experiment are illustrated in FIG. 13, which shows a dose response of signal obtained with the amount of DNA-binding protein added.

Example 7

Detection of Protein Binding to DNA by Inhibition of External Cleavage Reagent and a Labeled Oligonucleotide Probe.

Single stranded oligonucleotides PO4P50 (5 'PO4AGTT GAGGGGATCCCCAAGGGCGAAGGAACTCGACGTG GAGCCGTTTTT-aminoC6) (SEQ ID NO: 11) with a transcription factor binding sequence and a probe-capture sequence are coupled to beads through amino-C6 as described previously. Oligonucleotide PO4P50rev is hybridized with beads coupled to PO4P50 (1 pmole per 1000 beads) for 1 hour in transcription factor binding buffer(10 mM tris pH 7.5, 50 mM NaCl, 2 mM KCl, 2 mM MgCl2). Beads are then washed and resuspended to a concentration of 1000 beads/ul in transcription factor binding buffer. Binding reactions are then carried out by incubating 1000 beads with samples for 10 minutes at room temperature in a 20 ul volume of transcription factor binding buffer containing 0.35% BSA and 0.1–2 ug Poly dI-dC. Following the binding reaction, 20 ul of transcription factor binding buffer supplemented to 3 mM $MgCl_2$ containing 3 units of lambda exonuclease or an equivalent of lambda exonuclease storage buffer is added to appropriate reactions and incubated for 15 minutes at 37 degrees. 1pmole of biotin labeled single stranded probe DNA is then added to each reaction and hybridized with beads by heating to 95 C for 1 minute followed by cooling over a 30 minute period to reach room temperature. Following the hybridization of the probe to bead coupled DNA, assays are washed with 2×100 ul volumes of PBS pH 7.5 using a vacuum and filter plate. Beads are resuspended in 100 ul of 2 ug/ml SA-PE in PBS pH 7.5. Following a 10 minute incubation at room temperature, assays are analyzed using the Luminex 100 instrumentation.

Example 8

Detection of Protein Binding to DNA by Direct Labeling of Protein

Separately, 10 ug of control cell extract and 10 ug HeLa cell extracts spiked with 10 gel shift units of recombinant NF-kBP50 are suspended in 20 ul of labeling buffer (PBS pH 8.0). 0.5 mg of the water soluble form of N-hydroxysuccinimide-biotin (NHS-biotin) is added to each labeling reaction. Vortex and incubate for 2 hours at room temperature. Add 30 ul of transcription factor binding buffer (10 mM tris pH 7.5, 50 mM NaCl, 2 mM KCl, 2 mM MgCl2) to each labeling reaction and remove unincorporated NHS-biotin by desalting over a G-25 spin column. Incubate 1 gel shift unit of the desalted-labeled sampled with beads coupled to a hairpin detection molecule carrying an NF-KB P50 binding site. This incubation is carried out in a total volume of 20 ul transcription factor binding buffer containing 100 ng Poly dI-dC and 0.35% BSA fraction V. Following a 10 minute incubation at room temperature, add 80 ul of 2 ug/ml streptavidin-phycoerythrin in transcription factor binding buffer, incubate 10 minutes and analyze using the Luminex 100 instrumentation. Beads incubated with labeled hela cell extracts spiked with recombinant NF-kB P50 have Significant phycoerythin signal associated with their surfaces as compared to beads incubated with labeled HeLa cell nuclear extracts not spiked with recombinant NF-kb P50.

REFERENCES

1. Kido et al. *Clin Endocrinol Metab* 2001. Mar;86(3): 972–9.
2. Ferrannini et al. *Eur J Clin Invest* 1999. Oct;29(10): 842–52.
3. Zhao et al. *Mol Cell Endocrinol* 2001. May 25;177(1–2): 125–34.
4. Braddock. *Ann Med* 2001 Jul; 33(5):313–8.

5. Alizadeh et al. *Nature* 2000. Feb 3; 2000;403(6769): 503–11.
6. Takanami et al. *Tumour Biol* 2001. Jul–Aug; 22(4): 205–10.
7. Szybalski et al. *Gene* 1991. Apr;100: 13–26.
8. Kuo et al. *Ann N Y Acad Sci* 1994. Jul 29;726:223–34; discussion 234–5.
9. Elbrecht et al. *DNA* 1985 Jun;4(3):233–40.
10. Peck et al. *Nucleic Acids Res* 1994. Feb 11;22(3):443–9.
11. Brunet et al. *Anal Biochem* 1994. Oct;222(1):76–80.
12. Skulstad et al. *Virus Res* 1995 Aug;37(3):253–70.
13. Dignam et al., *Methods Enzymol* 1983.101:582–98.
14. Fujimaki et al., *Opinions in Structural Biology* 2001. Feb;11(1):26–32.
15. Morishita et al.,. *Pharmacol Ther* 2001. Aug;91(2): 105–14
16. Fruchart et al.,Am J Cardiol 2001 Dec 20;88(12 Suppl 1):24–9
17. Sporn et al., *Trends Mol Med* 2001. Sep:7(9):395–400.
18. Kersten et al.,. EMBO Rep 2001 Apr;2(4):282–6
19. Bamburger et al., *Cancer Research* 2000. Sep15;60(18) 5012–6.
20. Salti et al., *British Journal of Cancer* 1999. Sep; 81(1): 133–40.
21. Aoyagi et al., *Clin Cancer Res* 1998. Sep;4(9):2153–60.
22. Shen et al., *Biotechniques* 2002;32(5): 1168–1177.
23. Lam et al., American Biotechnology Laboratory July 2002.
24. Ausubel, F. M. et al. (1989) In: Current Protocols in Molecular Biology, Vol. 2, John Wiley and Sons, New York.
25. Juan et al., *Proc. Natl. Acad. Sci. USA*. 1993 April 1; 90 (7): 2584–2588.
26. Shen et al., *Biotechniques* 2002 32(5): 1168–1177.
27. Shalon et al., *Genome Research* 1996;6(7):639–645.
28. Fulton et al., *Clinical Chemistry* 1997;43: 1749–1756.

Those skilled in the art will recognize or be able to ascertain using no more than routine experimentation, many equivalents to the specific embodiments of the invention described herein. Such equivalents are intended to be encompassed by the following claims

What is claimed is:

1. A method for detecting a plurality of sequence specific DNA binding proteins, comprising:
   (a) contacting a plurality of detection duplexes, wherein each of said detection duplexes comprises (i) a first oligonucleotide comprising a distinguishable capture tag, wherein said capture tag is a nucleic acid sequence of natural nucleotides linked by natural linkages between nucleotides, and (ii) a second oligonucleotide that is complementary to said first oligonucleotide, wherein said second oligonucleotide comprises biotin, with a cellular or tissue extract suspected of containing a plurality of sequence specific DNA binding proteins for a time sufficient to permit sequence-specific binding between said duplex and said binding proteins;
   (b) contacting the mixture from step (a) with a cleavage reagent that is capable of cleaving said detection duplex, wherein cleavage of said detection duplex is inhibited by binding of said DNA binding protein to said duplex;
   (c) capturing the resulting mixture on a solid support by hybridizing said capture tag to a complementary oligonucleotide on said solid support and
   (c) detecting the inhibition of said cleavage by said DNA binding protein by detecting the presence or absence of biotin on said solid support.

2. The method according to claim 1, wherein said cleavage reagent is a sequence specific cleavage reagent.

3. The method according to claim 2, wherein said sequence specific cleavage reagent is a restriction endonuclease and said detection duplex comprises a restriction endonuclease recognition site.

4. The method according to claim 3, wherein said restriction endonuclease is a Type II restriction endonuclease and said restriction endonuclease site is a Type II restriction endonuclease recognition site.

5. The method according to claim 3, wherein said restriction endonuclease is a Type IIs restriction endonuclease and said restriction endonuclease site is a Type IIs restriction endonuclease recognition site.

6. The method according to claim 1 wherein said nuclease is an exonuclease.

7. The meted according to claim 1, wherein each detection duplex is captured at a predetermined position on a solid surface.

8. The method according to claim 1, wherein said cleavage reagent is a non-sequence specific cleavage reagent.

9. The method according to claim 1 wherein each detection duplex is captured on a distinguishable bead.

* * * * *

SEQUENCE LISTING

```
<160> NUMBER OF SEQ ID NOS: 11

<210> SEQ ID NO 1
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
agttgagggg atccccagga gcggcttatc ggtctattca actccctag ggg            53

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tcctggggat cccctcaact                                                20

<210> SEQ ID NO 3
<211> LENGTH: 45
<212> TYPE: DNA
<213> ORGANISM: Artificial Sequence
<220> FEATURE:
<223> OTHER INFORMATION: Description of Artificial Sequence: Synthetic
      HPNFKB65 hairpin detection duplex sequence

<400> SEQUENCE: 3
tatccaaggg gactttcccc tggcagggga aagtcccctt ggata                    45

<210> SEQ ID NO 4
<211> LENGTH: 20
<212> TYPE: DNA
<213> ORGANISM: Artificial Sequence
<220> FEATURE:
```

<223> OTHER INFORMATION: Description of Artificial Sequence: Synthetic
      hairpin oligonucleotide

<400> SEQUENCE: 4
tccaagggga ttccccagtg                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      hairpin oligonucleotide

<400> SEQUENCE: 5
tactggggaa tccccttgga                                              20

<210> SEQ ID NO 6
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
aaggatgagc gggggatccc aataggcggc tgcttatcgg tctat                  45

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ctattgggat ccccgctcat cctt                                         24

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
atagaccgat aagcagccgc                                              20

<210> SEQ ID NO 9
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
agttgagggg atccccagga gcggcttatc ggtctattca actcccctag ggg         53

<210> SEQ ID NO 10
<211> LENGTH: 20
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 10
tcctggggat cccctcaact                                                    20

<210> SEQ ID NO 11
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
agttgagggg atccccaagg gcgaaggaac tcgacgtgga gccgttttt                    49
```